United States Patent [19]

Isobe et al.

[11] Patent Number: 5,223,241
[45] Date of Patent: Jun. 29, 1993

[54] METHOD FOR EARLY DETECTION OF ALLOGRAFT REJECTION

[75] Inventors: Mitsuaki Isobe, Winchester; Ban A. Khaw, Milton, both of Mass.; Edgar Haber, Salisbury, N.H.

[73] Assignees: The General Hospital Corporation, Boston, Mass.; Bristol-Myers Squibb Company, Princeton, N.J.

[21] Appl. No.: 746,654

[22] Filed: Aug. 16, 1991

Related U.S. Application Data

[63] Continuation-in-part of Ser. No. 592,025, Oct. 1, 1990, abandoned.

[51] Int. Cl.$^5$ .................. A61K 49/02; A61K 43/00; C07K 15/28
[52] U.S. Cl. ..................... 424/1.1; 424/9; 530/391.3
[58] Field of Search .................... 424/1.1, 9

[56] References Cited

U.S. PATENT DOCUMENTS

| | | | |
|---|---|---|---|
| 4,864,020 | 9/1989 | Canle et al. | 424/1.1 X |
| 4,925,648 | 5/1990 | Hanssen et al. | 424/1.1 |
| 5,002,869 | 3/1991 | Schlossman et al. | 424/1.1 X |

*Primary Examiner*—Robert L. Stoll
*Assistant Examiner*—Matthew Zmurko
*Attorney, Agent, or Firm*—Sterne, Kessler, Goldstein & Fox

[57] ABSTRACT

The invention relates to a method of detecting early rejection of an allograft in a mammal by administering to the mammal a diagnostically effective amount of detectably labeled immunoglobulin or fragment thereof, wherein the immunoglobulin substantially accumulates at the site of allograft rejection. The method of the invention may also be used to monitor allograft rejection during immunosuppressive therapy in a mammal which has received an allograft or to localize areas involved in autoimmune disease or inflammation.

11 Claims, 24 Drawing Sheets

METHOD FOR EARLY DETECTION OF ALLOGRAFT REJECTION

This application is a continuation-in-part application of U.S. application Ser. No. 07/592,025 filed Oct. 1, 1990, now abandoned which disclosure is herein incorporated in its entirety.

FIELD OF THE INVENTION

This invention is related to non-invasive methods for early detection of allograft rejection as well as for the detection of autoimmune disease and inflammation.

BACKGROUND OF THE INVENTION

Transplantation of organs and tissues is an important aspect of treating end-stage organ failure and replacing damaged tissue. However, despite advances in this field, rejection continues to be a major obstacle to successful transplantation.

The antigenic differences between individual members of the same species are referred to as "alloantigens." When alloantigens are involved in rejection of allogeneic tissue grafts they are referred to as "histocompatibility antigens." The terms "major histocompatibility antigens" and "major histocompatibility complex" (MHC) refer to the products of a single closely linked region of genes.

The MHC gene products are displayed on cell surfaces and are an important barrier to successful allotransplantation. In humans, the MHC is, by international agreement, referred to as "HLA." (Carpenter, C. B., in *Harrison's Principles of Internal Medicine*, ed. E. Braunwald et al., (McGraw-Hill, New York, 1987, page 337.) The individual letters in this abbreviation have a variety of meanings, including "Human Leukocyte (or Lymphocyte) Antigen" and "Histocompatibility Locus Antigen."

Graft rejection is the consequence of the host immune response to histocompatibility antigens expressed by the graft tissue. Allografts generally survive for a period of days to weeks, but may subsequently become inflamed and infiltrated with lymphocytes and monocytes. The graft tissue eventually becomes necrotic, and in the case of skin transplant, is sloughed from the skin. However, in the case of a vital organ such as the heart, the sequelae to tissue rejection can be fatal to the recipient.

In humans, cardiac transplants are closely monitored for signs of graft rejection. Commonly, this entails the performance of endomyocardial biopsies on cardiac transplant recipients weekly for the first 8 weeks after transplant, every other week for the next 8 weeks, monthly for the next year, and every 3-4 months for the remainder of the patient's life (Ahmed-Ansari, A. et al., *Transplantation* 45:972-978 (1988)).

The biopsied tissue is studied histologically for indicia of tissue rejection. A grade of rejection is determined on the basis of the degree of infiltration by leukocytes and cell necrosis. (Ahmed-Ansari et al., supra). It is believed that some of the infiltrating lymphocytes function as killer cells and attack graft tissues. Infiltrating lymphocytes produce lymphokines such as interferons, and interferon gamma is a potent stimulator of MHC induction. Expression of MHC antigens by the graft tissue is enhanced by the lymphokines, and graft cells become more sensitive to killer cells (Lindahl, P. et al., *Proc. Nat. Acad. Sci.* 73:1284-1287 (1976); Heron, I. et al., *Proc. Nat. Acad. Sci.* 75:6215-6219 (1978)).

In view of the discomfort and risks associated with repeated biopsy, there is a need for a non-invasive method of detecting early stages of allograft rejection.

SUMMARY OF THE INVENTION

Compositions and methods are provided for detection of allograft rejection in a mammal. A diagnostically labeled immunoglobulin molecule, or fragment thereof, capable of binding to a MHC antigen expressed by the graft tissue, is administered to the mammal. Graft rejection is detected as the accumulation of labeled immunoglobulin at the site of the graft. The invention also finds use in the detection and localization of autoimmune disease.

BRIEF DESCRIPTION OF THE FIGURES

FIG. 19 shows the extent of necrosis.

DETAILED DESCRIPTION OF THE INVENTION

Figure 1A:
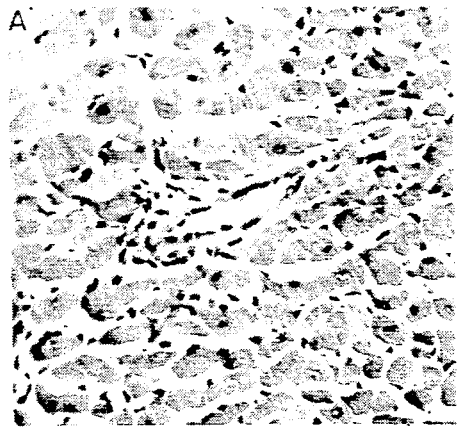
FIG. 1: Photomicrographic sections of ectopic cardiac allografts. A, mild rejection with focal lymphocytic cellular infiltration; B, moderate rejection with confluent lymphocytic infiltration; C, moderate rejection with focal myocyte necrosis along with lymphocytic infiltration; D, severe rejection with extensive myocyte necrosis, cellular infiltration and bleeding. (Original magnification ×400).
Figure 1B:
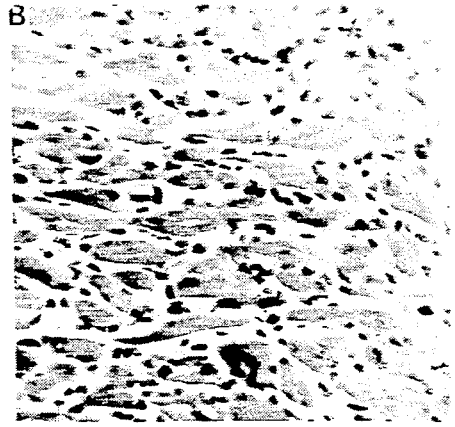
Figure 1C:
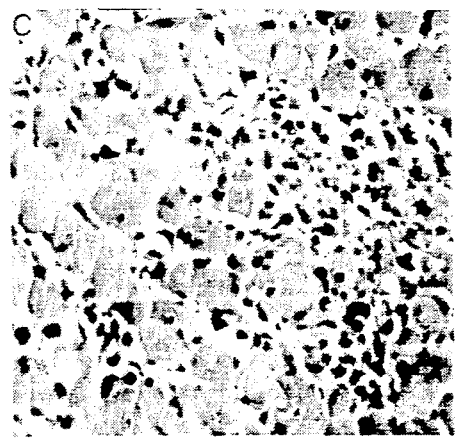
Figure 1D:
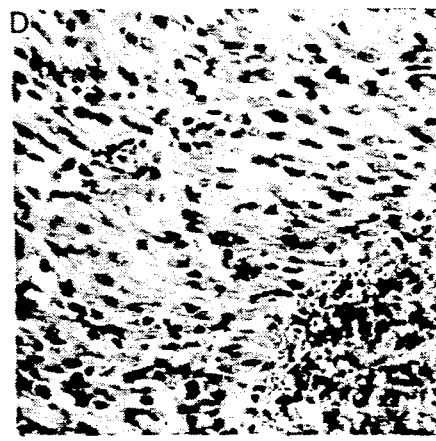

The invention is drawn to compositions and methods for the detection of MHC class 2 antigens. Class 2 antigens are involved in antigen presentation on macrophages and dendritic cells and play an essential role in inducing the immune response. Further, the expression of class 2 antigens is enhanced in rejecting transplanted organs or tissues, tissues undergoing autoimmune injury, viral disease, and the inflammatory status. The present invention utilizes labeled antibodies or antibody fragments as a noninvasive technique for the detection and quantitation of class 2 antigens as an early indicator of allograft rejection as well as the localization of autoimmunity.

An important characteristic of immunologically-mediated organ and tissue rejection responses is the presence of lymphocyte infiltrates in the transplanted tissue. Lymphocytes are capable of mediating a range of immunological effects. Many of the lymphocytes present in the transplanted tissue are believed to be sensitized against antigens expressed by the donor transplanted tissue. Following activation, these lymphocytes induce cytocidal effects against cells of the transplanted tissue. The antigens against which many of the lymphocytes are sensitized are the major histocompatibility complex (MHC) antigens.

The MHC of the mouse has been studied extensively, primarily because highly inbred strains of mice (genetically identical individuals) are available. The mouse MHC, designated histocompatibility-2 (H-2), is homologous to the MHC complex of humans, HLA. In both species, the antigens of the MHC play a similar role in allowing the immune system to distinguish between self and non-self cells and tissues.

Human and mouse MHC antigens are divided into three classes, class I, class II and class III, on the basis of functional differences. Human and mouse class I MHC molecules share about 70 to 75 percent of their amino acids (J. Klein, *Immunology* (John Wiley & Sons, 1982), p. 295).

Because the HLA and H-2 antigens play homologous roles within the immune systems of, respectively, humans and mice, the H-2 complex has long been used as a model system for studying the MHC in general. Work performed using inbred strains of mice has greatly advanced the ability to understand mechanisms of tissue rejection in humans. Thus, results of transplantation studies in mice have immediate and direct applicability to human organ and tissue transplants.

A fundamental occurrence in the tissue rejection process in both mice and humans is the enhanced expression of MHC antigens by the transplanted tissue. In heart transplants, for example, the vascular endothelial cells and antigen-presenting cells of the graft express certain MHC antigens. These antigens may cause the initial sensitization of host lymphoid cells. (Ahmed-Ansari, A. et al., *Transplantation* 45:972-978 (1988)).

Following transplant in a human, the patient's progress is often monitored by obtaining biopsy specimens of the transplanted tissue. In the case of human heart transplants, this process may be repeated frequently at some risk and discomfort to the patient.

If histological evidence of rejection is obtained by examination of the biopsy specimen, the patient is often treated with immunosuppressive drugs such as cyclosporine and steroids. However, the histological changes on which this treatment is based do not necessarily signal graft rejection. For example, the leukocytes may be present as a result of a previous inflammatory episode, or a result of cyclosporine therapy. Thus, histological examination of a biopsy may not accurately reflect the status of the graft.

There is evidence that expression of MHC antigens in human heart transplants precedes development of tissue necrosis that can be detected by histological examination of biopsies (Ahmed-Ansari, A. et al., supra). Detection of MHC expression by the graft tissue therefore affords an improved and early noninvasive method for measuring graft rejection.

The absence of detectable levels of MHC-Class II gene products on human cardiac myocytes from uninflamed heart tissue has been demonstrated. (Ahmed-Ansari, A. et al., *Fed. Proc.* 46:946 (1987)). MHC Class I antigens are also expressed at low or undetectable levels on cardiac myocytes. (Ahmed-Ansari, A. et al., *Am. J. Cardiovasc. Pathol.* 2:193-210 (1988)). MHC Class I antigens are expressed at low levels on donor endothelial or interstitial cells. It is believed that recipient lymphoid cells are initially sensitized by donor specific MHC antigens on such cells.

This initial sensitization is followed by a marked increased in the level of MHC Class I and Class II antigens on cardiac myocytes (Ahmed-Ansari, A. et al. (1988), supra). The expression of MHC Class I and Class II antigens was first demonstrated using immunoperoxidase staining techniques. However, using the more objective radioimmunoassay techniques, Sell et al. found that histological evidence of rejection episodes with scores of 3 or greater on sequential heart biopsies of six patients was always preceded by a marked increase in MHC RIA indexes. (Sell, K. W. et al., *J. Heart Transplantation* 7:407-418 (1988)).

In a more extensive study of MHC antigen expression by transplanted cardiac tissue, Steinhoff et al. reported that in 57 of 78 rejection episodes in 33 patients, Class I MHC antigens were induced on myocyte membranes. Class I MHC antigen induction could be reversed within 1 to 3 weeks by steroid treatment for rejection. Class II antigen induction on capillary endothelia was also noted during rejection episodes. (Steinhoff, G. et al., *J. Heart Transplantation* 8:360-370 (1989)).

These studies were limited by the need to biopsy the transplanted cardiac tissue in order to evaluate MHC antigen expression and histological indicia of rejection.

According to the methods of this invention, expression of MHC antigens is detected in a non-invasive manner using immunoglobulins, or fragments thereof, capable of recognizing and binding to the antigen. The antibodies may be labeled to permit their detection following administration to a mammal.

As used herein, the term "mammal" is meant to include both human and non-human mammals.

The term "antigen" means generally a protein or non-protein substance which is expressed on the surface of mammalian cells. As used herein, the term "antigen" means a component of the major histocompatibility complex, or an immunogenic fragment thereof, particularly MHC class 2 antigens.

The term "immunoglobulin or a fragment thereof" as used herein is meant to include intact immunoglobulin molecules as well as fragments thereof, such as, for example, the Fab and F(ab)$_2$ fragments, which are capable of binding to antigenic determinants of the graft tissue.

The terms "diagnostically labeled" and "diagnostically conjugated to a detectable label" mean that the immunoglobulin has attached to it a diagnostically detectable label.

The term "diagnostically detectable label" means a detectable chemical moiety such as a radionuclide or a paramagnetic isotope, such labels being capable of visualization with an appropriate detection instrument.

The immunoglobulins of the invention can be polyclonally or monoclonally derived, an important factor being that the immunoglobulin used is directed to a major histocompatibility antigen (MHC) expressed by the graft tissue.

If desired, polyclonal immunoglobulin preparations may be prepared from the blood of immunized individuals of the desired species following immunization with MHC antigen, followed by harvesting of the blood and processing it according to defined techniques. A distinct advantage of non-specific, polyclonal immunoglobulin preparations is that by preparing immunoglobulin from the same species into which it will be injected, immune reactions across species barriers are prevented and repeated injections of the same product are less likely to cause side-effects.

Monoclonal immunoglobulins which can be used according to the method of the invention can be prepared using hybridoma fusion techniques (Kohler et al., *European Journal of Immunology* 6:292, 1976; U.S. Pat. Nos. 4,609,893; 4,713,325; 4,716,111; 4,716,117; and 4,720,459) or can be derived from known secreting myeloma cell lines such as those available from depositories such as the American Type Culture Collection. General reviews of "humanized" chimeric antibodies are provided by Morrison, S. L., *Science* 229:1202-1207 (1985) and Di. T.V., et al., *Bio Techniques* 4:214 (1986) as well as the reference cited therein. See also Jones et al., *Nature* 321:525-552 (1986); Verhoeyan et al., *Science* 239:1534 (1988); and Beidler et al., *J. Immunol.* 141:4053-4060 (1988).

Alternatively, monoclonal antibodies useful in practicing the invention may be prepared in the following manner, using human MHC antigens purified from human lymphocytes:

Collected lymphocytes are lysed with detergent, such as Triton-X 100. The supernatant from the centrifugation is passed through an immunoaffinity column containing antibody against human MHC (commercially available from Becton-Dickinson). After washing the column, bound MHC antigens are eluted from the column in conditions which dissociate the antigen-antibody interaction. After dialysis and concentration, purified MHC antigens are used for immunization.

Monoclonal antibodies can be prepared according to the methods of standard hybridoma technique (Kohler et al., *European Journal of Immunology* 6:292 (1976)). Screening for anti-MHC antibody is performed by a two-stage complement-mediated cytotoxicity assay (Ozato et al., *Journal of Immunology* 124:533 (1980)).

In detecting early graft rejection in a mammal, the detectably labeled immunoglobulin is advantageously given in a dose which is diagnostically effective. The term "diagnostically effective" means that the amount of detectably labeled immunoglobulin administered is sufficient to enable detection of the site of the graft when compared to the background signal.

Generally, the dosage of detectably labeled immunoglobulin for diagnosis will vary depending on considerations such as age, condition, sex, extent of disease, and type of transplant in the patient, and affinity and specificity of the antibody. The dosage will also depend on counterindications, if any, and other variables, to be adjusted by the individual physician. Dosage can vary from 0.01 mg/kg to 2,000 mg/kg, preferably 0.1 mg/kg to 1,000 mg/kg.

The labeled immunoglobulins or fragments of the present invention can be administered by any method known in the art with the major consideration being a method suitable to saturate the area of interest. Typical administrations include parentally by injection, rapid infusion, nasopharyngeal absorption (intranasopharyngeally), derma absorption, or orally. The compositions may alternatively be administered intramuscularly, or intravenously. Compositions for parenteral administration include sterile aqueous or nonaqueous solutions, suspensions, and emulsions. Examples of nonaqueous solvents are polypropylene glycol, polyethylene glycol, vegetable oils such as olive oil, and injectable organic esters such as ethyloleate. Carriers or occlusive dressings can be used to increase skin permeability and enhance antigen absorption.

There are many different labels and methods of labeling known to those of ordinary skill in the art. Examples of the types of labels which can be used in the present invention include radioactive isotopes and paramagnetic isotopes.

Those of ordinary skill in the art will know of other suitable labels for binding to the immunoglobulins used in the invention, or will be able to ascertain such, using routine experimentation. Furthermore, the binding of these labels to the immunoglobulin can be done using standard techniques common to those of ordinary skill in the art.

For diagnostic in vivo imaging, the type of detection instrument available is a major factor in selecting a given radionuclide. The radionuclide chosen must have a type of decay which is detectable for a given type of instrument. In general, any conventional method for visualizing diagnostic imaging can be utilized in accordance with this invention.

Another important factor in selecting a radionuclide for in vivo diagnosis is that the half-life of a radionuclide be long enough so that it is still detectable at the time of maximum uptake by the target, but short enough so that deleterious radiation upon the host is minimized. Ideally, a radionuclide used for in vivo imaging will lack a particulate emission, but produce a large number of photons in a 140–200 keV range, which may be readily detected by conventional gamma cameras.

For in vivo diagnosis, radionuclides may be bound to the immunoglobulin either directly, or indirectly by using an intermediary functional group. Intermediary functional groups which are often used to bind radioisotopes which exist as metallic ions to immunoglobulins are diethylenetriaminepentaacetic acid (DTPA) and ethylenediaminetetraacetic acid (EDTA). Typical examples of radionuclides which can be bound to immunoglobulins are $^{99m}Tc$, $^{123}I$, $^{111}In$, $^{131}I$, $^{97}Ru$, $^{67}Cu$, $^{67}Ga$, $^{125}I$, $^{68}Ga$, $^{72}As$, $^{89}Zr$, and $^{201}Tl$.

The immunoglobulins used in the method of the invention can also be labeled with paramagnetic isotopes for purposes of in vivo diagnosis. Elements which are particularly useful (as in Magnetic Resonance Imaging (MRI) techniques) in this manner include $^{157}Gd$, $^{55}Mn$, $^{162}Dy$, $^{52}Cr$, and $^{56}Fe$.

In order to practice the invention, it is preferable to use monoclonal antibodies directed against MHC antigens. Monoclonal antibodies to human MHC antigens are commercially available. For example, antihuman MHC class II HLA-DR monoclonal antibody reagent (clone L-243) is available from Becton-Dickinson, Mountain View, Calif. Antihuman MHC class I monoclonal antibody reagent W6/32 (Sero-tec Labs., Indianapolis, Ind.) may also be used.

The method of the invention can also be used to monitor the course of immunosuppressive therapy. Labeled antibodies can be administered before, during and after therapy, and the imaging results will indicate the absence or extent of rejection as a function of the immunosuppressive therapy. Monitoring of an allograft would otherwise require repeated biopsies of the allograft tissue.

The compositions and methods of the invention further find use in the detection and localization of autoimmune diseases. In this manner, labeled immunoglobulins directed against MHC, class 2 antigens can be administered to an individual suspected of having an autoimmune disease. Localization of the label would indicate areas of MHC, class 2 antigen expression possibly involved in autoimmune disease. This method would also be useful to monitor the progression of an autoimmune disease. Modes and rates of administration are as discussed above in general terms.

The invention may also be utilized to localize internal areas of inflammation or disease, particularly viral disease. In the same manner as discussed above, class 2 antigens can be detected which are enhanced in viral disease and inflammatory status. (See generally, McMichael et al., *Nature* 270:524 (1977), and Appelyard et al., *Lancet* 1:361 (1985).

The above disclosure generally describes the present invention. A more complete understanding can be obtained by reference to the following specific example which is provided herein for purposes of illustration only, and is not intended to be limiting unless otherwise specified.

EXPERIMENTAL

Example 1

Animals

Male, inbred B10D2 and B6AF1 mice were obtained from the Jackson Laboratory (Bar Harbor, Me.). CD-1 mice were purchased from Charles River Breeding Laboratory (Boston, Mass.).

Organ Grafting

Heterotopic cardiac transplantation was performed in 75 mice. The B10D2 donor, B6AF1 recipient combination was used for 63 allografts. B10D2 (n=5), B6AF1 (n=4), or CD-1 (n=3) hearts were also isografted. Hearts were transplanted to the abdomen of the recipients as primary vascularized grafts by the microvascular technique described by Ono et al. (Ono, K., et al., *J. Thorac. Cardiovasc. Surg.* 57:225-229 (1969)) and Corry et al., (Corry, R. J., et al., *Transplant.* 16:343-350 (1973)), with some modifications.

Donor Preparation: Mice (15-25 g) were anesthetized with 3.6% chloral hydrate i.p. at a dose of 0.1 mL/10 g, and the abdominal skin was cleaned with 70% ethanol. The operation was performed under clean but nonsterile conditions. After a midline abdominal incision had been made and the abdominal aorta was cut to allow the animal to exsanguinate, the incision was extended cephalad to open the chest widely. The following procedures were performed under an operating microscope. The inferior vena cava was isolated and 0.5 to 1 mL of a cold, 7.5% solution of heparin in cardioplegia solution (7 g of glucose and 24 mEq of potassium chloride dissolved in 1 L of lactated Ringer's solution, pH 7.8 adjusted by Tris) was intermittently infused into the vessel with a 30 gauge needle. The inferior and superior vena cava were then ligated with 6-0 silk and cut away. The hili of the right and left lungs were ligated and transected independently and the aorta and pulmonary arteries were separated and cut with microscissors. A ligature was then placed around the mass of pulmonary veins. The heart, which was at that point detached from the chest wall, was placed in cold (4° C.) cardioplegia solution. The whole procedure was completed within 10 minutes.

Recipient preparation: The recipient mice were prepared as described above. The abdomen was shaved and a midline abdominal incision was made. The intestine was then exteriorized and wrapped with wet gauze. The abdominal aorta and inferior vena cava were gently separated below the branching of the renal vessels using cotton-tipped applicators and forceps. All small lumbar vessels were ligated with 6-0 silk. Proximal control of the inferior vena cava was obtained by ligature with 6-0 silk and the abdominal aorta was secured with a Yasargil artery clamp. Distal control was established en masse with 6-0 silk ligature. After closely adjacent venotomy and aortotomy were effected by microscissors, the donor heart was placed within the abdominal cavity. An end-to-side anastomosis was then made by running suture with 10-0 nylon strand (Ethilon) tipped with a BV75-3 needle. After the anastomoses had been completed, the distal and proximal ligatures and a clamp were loosened in this order slowly and carefully. At this point the grafted hearts became pink and began to contract within a few seconds of reperfusion, after which rhythmic contraction was restored. Warm saline was then dripped onto the graft. After the confirmation of continuous strong beats in the graft, the abdominal wall was closed with 6-0 silk. The animal was then warmed under a heat lamp. The ischemic time was defined as the interval between the injection of cardioplegia solution into the donor heart and reperfusion.

Experimental Groups

Cyclosporine (Sandoz, Inc., Basel, Switzerland) (15 mg/kg) was injected subcutaneously daily beginning on the day of operation in 26 allografted mice. Four of 37 allografted mice without cyclosporine, 3 of 26 mice with cyclosporine, and 1 of 12 isografted mice died within 2 days after transplantation and were excluded from the analysis.

Heart Beat

The function of the transplanted hearts was assessed daily by direct palpation, and mechanical activity was graded independently by two examiners. Our preliminary experience and a report from another laboratory (Corry, R. J., et al., *Transplant.* 16:343-350 (1973)) show that a sharp decline in the intensity of the cardiac impulse is a reliable sign of rejection. The quality of the heart beats was graded from 0 to 4+ (4+ being optimal and 0 complete arrest). Grades 4+ and 3+ were considered normal. Grades 2+, 1+, and 0 were interpreted as signs of rejection.

Scintigraphy

The preparation of antimyosin monoclonal antibody 2G42D7 has been reported previously (Khaw, B. A., et al., *Hybridoma* 33:11-23 (1984)). Diethylenetriaminepentaacetic acid (DTPA) was covalently attached to the antibody according to the procedures of Krejcarek and Tucker (Krejcarek, G. E., et al., *Biochem. Biophys. Res. Comm.* 77:581-585 (1977)) and Khaw et al. (Khaw, B. A., et al., *Circulation* 74:501-508 (1986); Khaw, B. A., et al., *J. Nucl. Med.* 28:76-82 (1987)). DTPA coupled to antimyosin antibody was labeled with indium-111 (Khaw, B. A., et al., *J. Nucl. Med.* 28:76-82 (1987)). Mice were randomly chosen for scintigraphy from 2 to 15 days after the transplantation. Approximately 100 $\mu$Ci of labeled antimyosin was injected into the tail vein 24 to 48 hours before imaging. Scintigraphy was performed after intraperitoneal injection of chloral hydrate. Planar images were obtained with a gamma camera (Ohio Nuclear 100) equipped with a 3 mm diameter pinhole collimator. One hundred thousand to 300,000 counts were obtained in a presetting of 5 minutes for each image.

Tissue Analysis

Mice were killed after scintigraphy and venous blood was withdrawn from the inferior vena cava. The autologous heart, transplanted heart, liver, spleen, kidneys, lungs, and small intestine were excised. Both hearts were washed thoroughly with saline and immersed in 10% formalin. Each organ was weighed and the biodistribution of radioactivity in the organ was determined by gamma scintillation counting. Localization was expressed as the percent injected dose per gram of wet tissue (% dose/g). The ratio of dose/g of the grafted heart (G) to that of the autologous heart (A) was determined for each mouse and designated as G/A. We regarded indium-111 labeled antimyosin activity in the autologous heart as background antibody uptake by normal myocardium.

Duration of Ischemia and Antimyosin Uptake

The duration of ischemia in the donor heart has been shown to be a crucial factor of myocyte necrosis in the murine ectopic heart transplantation model (Lurie, K. G., et al., *J. Thorac. Cardiovasc. Surg.* 84:122-129 (1982); Smith, J. A., et al., *Surgery* 101:86-90 (1987); Blanchard, J. M., et al., *Microsurg.* 6:169-174 (1985)). The effect on antimyosin uptake of myocyte necrosis due to ischemia during operation was investigated in 20 isografted mice (B10D2 or B6AF1). Heart transplantation was performed as described above. Mice were randomly assigned to 4 groups (A, B, C, and D) of five each. Reperfusion was performed at 30 minutes after resection of the donor hearts in group A, at 60 minutes in group B, at 90 minutes in group C, and at 120 minutes in group D. Five minutes after reperfusion the mice were injected with approximately 100 pCi of indium-111 labeled antimyosin. Fifteen minutes later, grafted and autologous hearts were resected and the G/A ratio was determined for each mouse.

Histological Examination

Grafted and autologous hearts were embedded in paraffin and stained with hematoxylin and eosin. The samples were submitted for blinded histopathologic evaluation and were scored on a scale of 0-3 for degree of rejection as follows: 0=normal, 1=mild rejection, 2=moderate rejection, and 3=severe rejection. The mice with moderate rejection were divided into two groups according to the presence or absence of myocyte necrosis.

Statistical Analysis

The Bonferroni method was used for multiple comparisons (Wallenstein, S., et al., *Circ. Res.* 47:1-9 (1980)). A $p>0.05$ was considered nonsignificant in comparisons between multiple groups of data. All data were expressed at the mean ± standard deviation. Linear regression was computed by the least scares method.

RESULTS

Relationship Between Time of Ischemia During Operation and Indium-111 Antimyosin Uptake The G/A ratio increased in proportion to time of ischemia. The G/A ratio was 1.3±0.3 in group A (30 minutes of ischemia), 1.5+0.3 in group B (60 minutes of ischemia), 2.3±0.4 in group C (90 minutes of ischemia) (p 0.01 versus both A and B), and 3.7±0.8 in group D (120 minutes of ischemia) (p 0.001 versus A, p 0.01 versus both B and C). The G/A in group A and group B was significantly lower than that in groups C and D, although there was no statistical difference between groups A and B. Thus, we considered an ischemia time of more than 60 minutes as having a significant effect on antimyosin uptake in grafts. On the basis of these observations, we excluded 9 grafts for which the ischemia time during operation was longer than 60 minutes. Some of these excluded mice showed abnormally high antimyosin uptake in comparison with their histological degree of rejection. This exclusion criterion reduced the study groups to 30 allografts without cyclosporine, 19 with cyclosporine, and 9 isografts.

Histopathology

Figure 2:
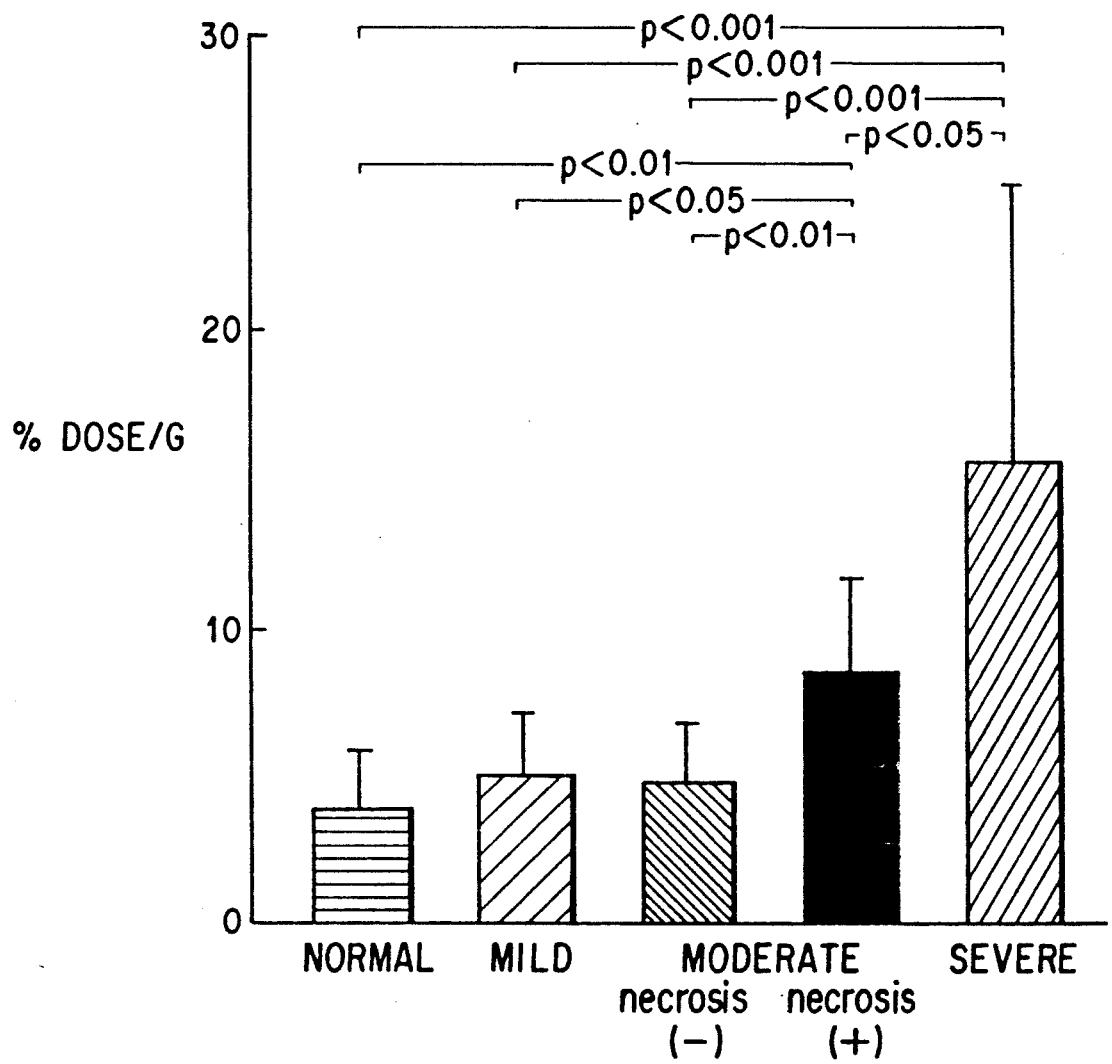
FIG. 2: Percent dose of antimyosin per gram of grafted heart (% dose/g) compared with histological degree of rejection. Mice with moderate rejection were divided into two groups according to the presence or absence of myocyte necrosis. The % dose/g in mice that showed moderate rejection with myocyte necrosis is significantly greater than the % dose/g in those with normal, mild, and moderate rejection without necrosis. Mice with severe rejection showed a greater % dose/g than any other group.
Figure 3:
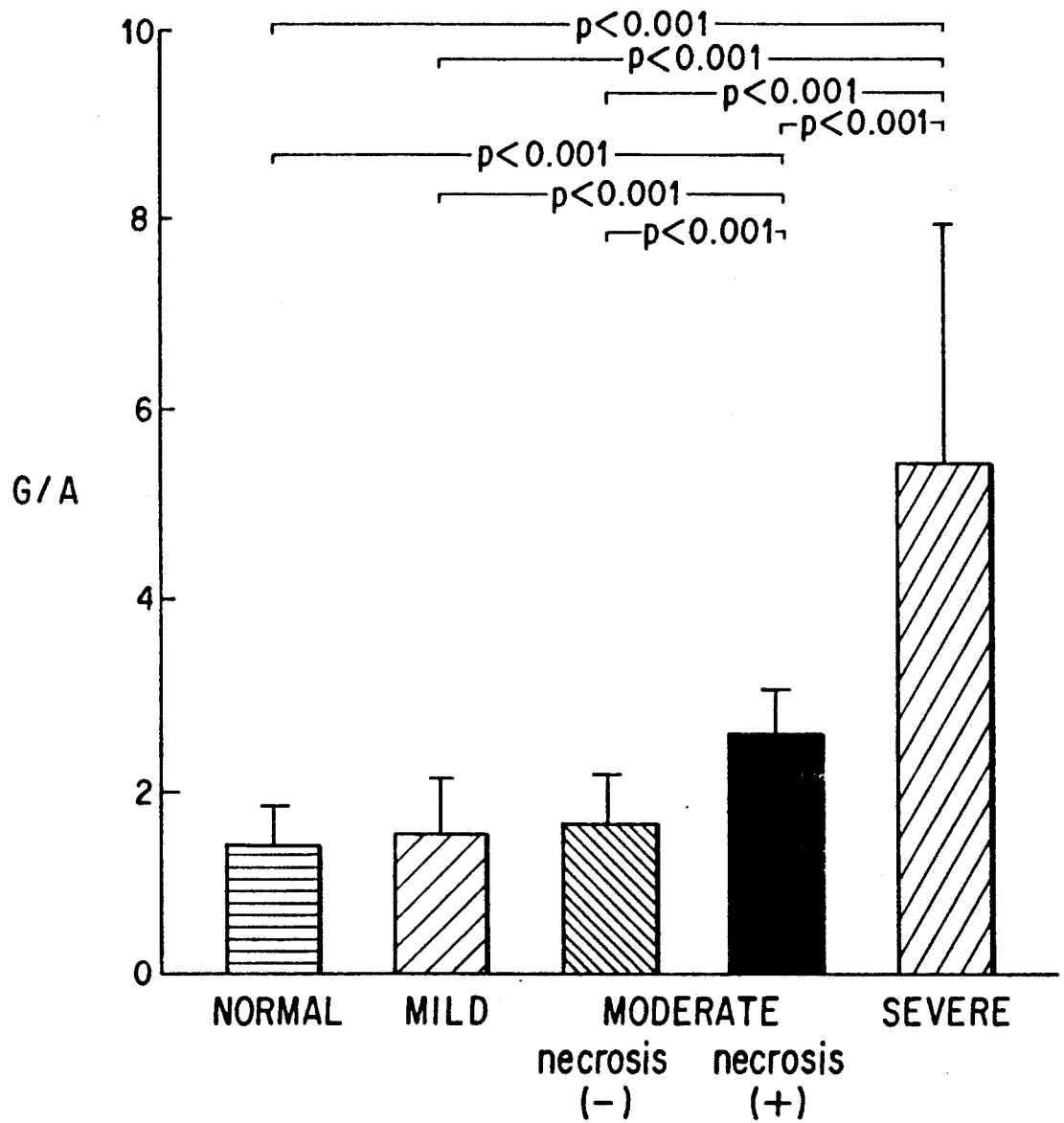
FIG. 3: The ratio of percent dose of antimyosin (% dose/g) of grafted heart (G) to that of autologous heart (A), G/A, compared with histological degree of rejection. The G/A ratio is greater in severe rejection and in moderate rejection with myocyte necrosis than in other groups that show no myocyte necrosis.

A broad spectrum of histological findings was present among the 49 allografts, ranging from nearly normal to severe rejection (FIG. 1). Regardless of the time after transplantation and the presence or absence of cyclosporine therapy, antibody uptake increased with increasing degree of severity of rejection (Table 1, FIGS. 2 and 3). Mice with mild rejection or moderate rejection in the absence of necrosis showed no statistical increase in G/A or % dose/g in comparison with mice deemed normal by histology. But mice with severe rejection or moderate rejection with the presence of necrosis showed significant increases in both G/A and % dose/g of grafted heart when compared with mice with no, mild, or moderate rejection without necrosis.

A G/A equal to or greater than 1.95 detected 100% (26/26) of the grafts with severe rejection or moderate rejection with histological evidence of necrosis. In contrast, G/A was less than 1.95 in 91% (29/32) of the grafts without histological evidence of necrosis.

Three of the allografts among the 19 mice that were treated with cyclosporine showed histologically severe rejection. Both G/A (3.79, 2.78 and 7.14) and % dose/g of grafted heart (14.7, 10.3 and 11.15, respectively) in these 3 mice were greater than those of any other allografted mice with cyclosporine therapy or those of isografted mice. In contrast, the G/A of mice treated with cyclosporine but without histological evidence of necrosis was no more than 1.81, which was as low as that of the isografted mice.

Time Course of Indium-111 Antimyosin Uptake

Figure 4:
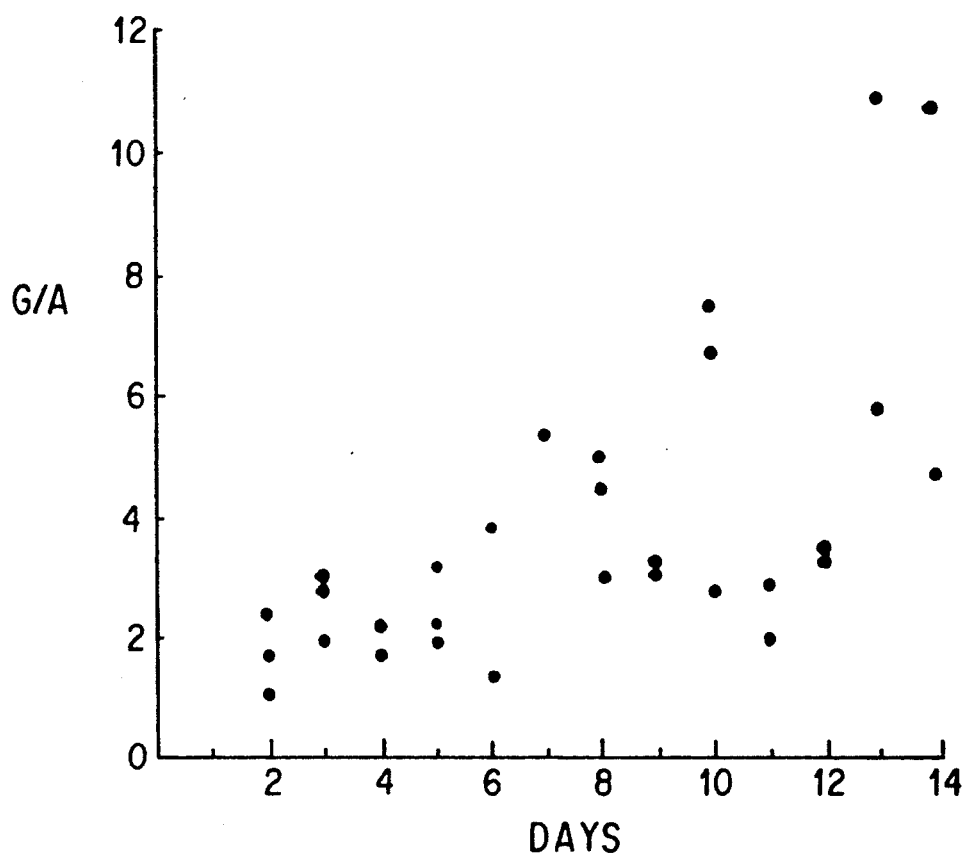
FIG. 4: The ratio of percent dose of antimyosin (% dose/g) of grafted heart (G) to that of autologous heart (A), G/A, in nontreated, allografted mice plotted against days after transplantation. The accumulation of labeled antimyosin in allografts increases progressively ($r=0.64$, $p<0.001$).
Figure 5:
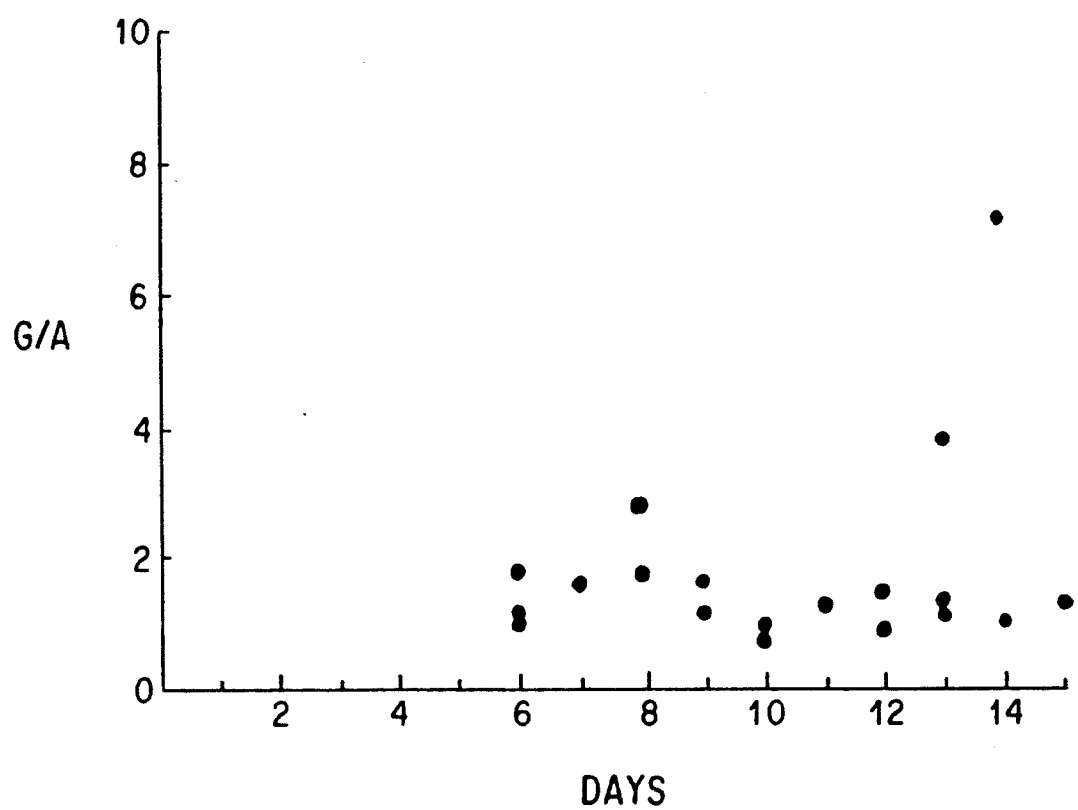
FIG. 5: Time course of the ratio of percent dose of antimyosin (% dose/g) of grafted heart (G) to that of autologous heart (A), G/A, in allografted mice treated with cyclosporine (15 mg/kg per day). Three mice with a G/A of more than 2.0 showed histologically severe rejection, whereas the other 16 with a G/A of less than 1.81 showed no histological evidence of myocyte necrosis due to rejection.

The G/A increased progressively with time in allografted mice that did not receive cyclosporine therapy ($r=0.64$, $p<0.001$) (FIG. 4). In contrast to the progression in the G/A ratio in these allografted mice, the isografted mice showed no significant increase in the G/A ratio as late as 14 days after transplantation. FIG. 5 shows the time course of the G/A ratio in cyclosporine-treated allografts.

Allografted animals not treated with cyclosporine were divided into three groups according to the time between transplantation and tissue counting: 2-4 days (n=8), 5-9 days (n=11), and 10-14 days (n=11). As shown in Table 2, the G/A ratio in the group that was killed early (2-4 days) was not significantly different from the isografted group. But in the 5-9 day and 10-15 day groups, the G/A ratio was significantly greater than that of the isografted animals ($p<0.001$ and $p<0.01$, respectively).

Heart Beat

Figure 6:
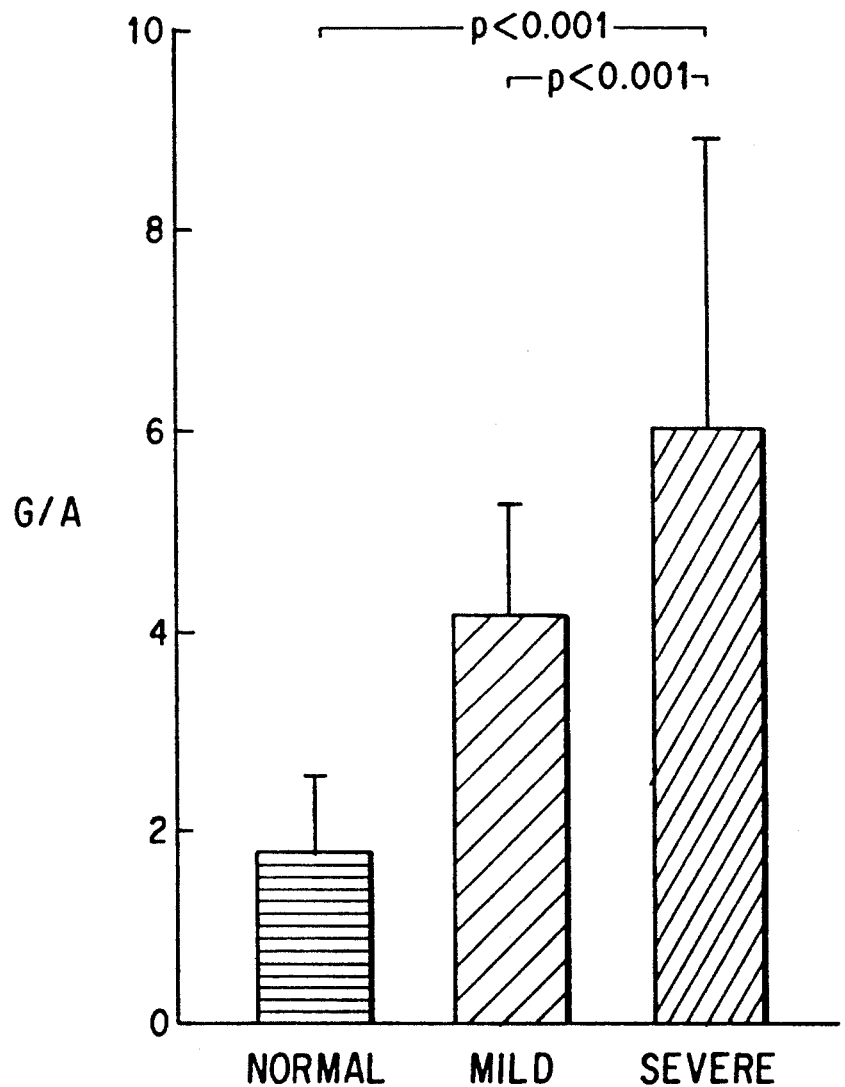
FIG. 6: The ratio of percent dose of antimyosin (% dose/g) of grafted heart (G) to that of autologous heart (A), G/A, compared with myocardial contractility. The G/A increases according to the deterioration of mechanical activity of the allografts.
Figure 7:
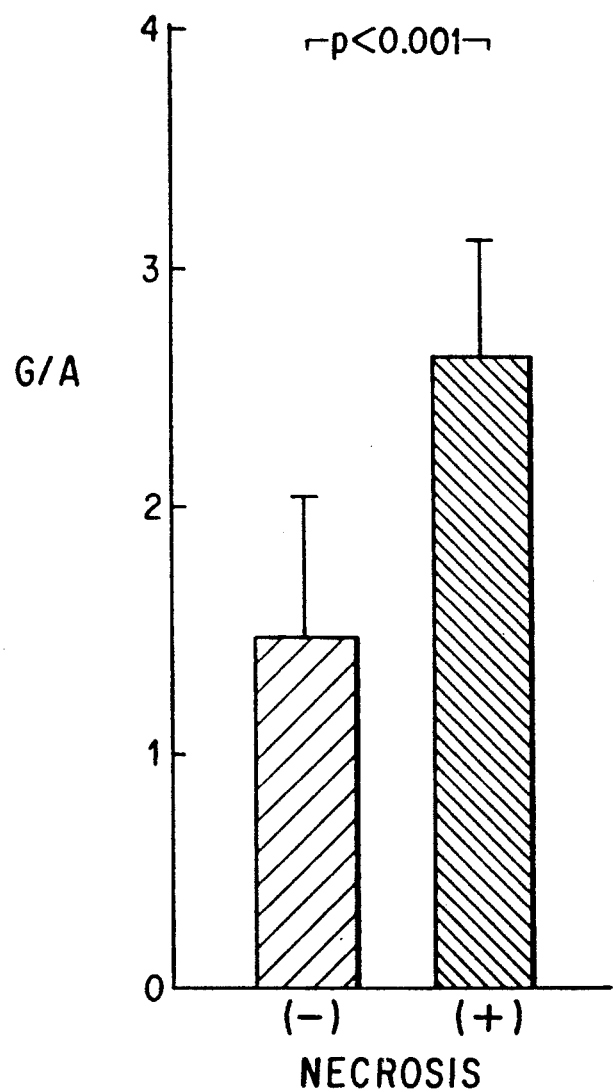
FIG. 7: The ratio of percent dose of antimyosin (% dose/g) of grafted heart (G) to that of autologous heart (A), G/A, in mice that show normal allograft contraction compared with G/A in mice with and without histological evidence of myocyte necrosis. Eight of 24 mice with apparently normal mechanical activity had evidence of myocyte necrosis; the G/A in these 8 mice is significantly greater than the G/A in the remaining 16 mice that did not show myocyte necrosis.
Figure 8:
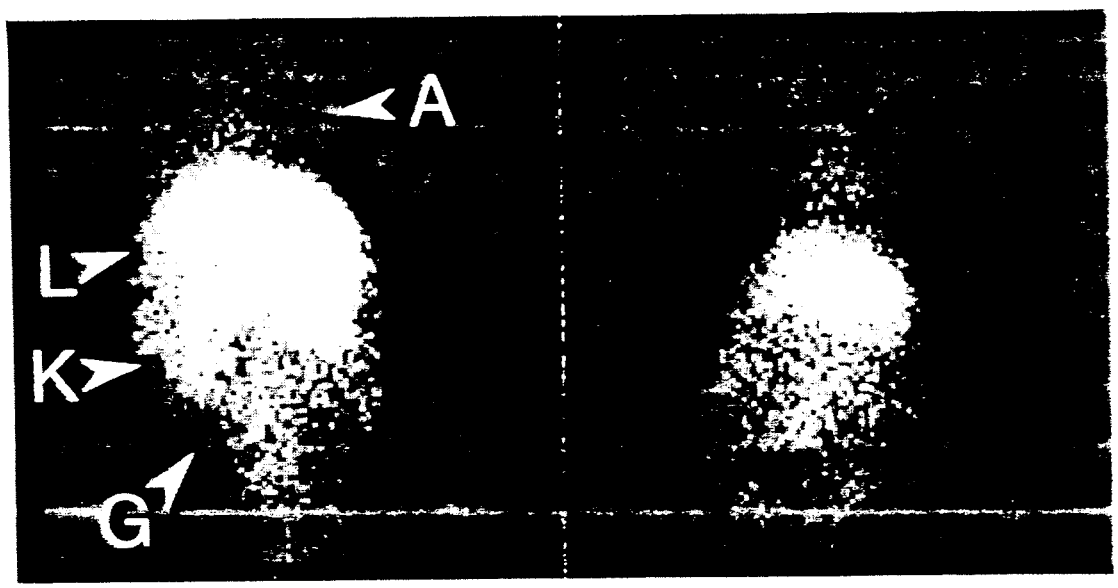
FIG. 8: Scintigrams of nontreated, allografted mice 3 days (left panel) and 4 days (right panel) after transplantation. The ratios of percent dose of antimyosin (% dose/g) of grafted heart to that of autologous heart determined immediately after scintigraphy are 1.7 and 1.9, respectively. Faint uptake is visible in the right panel in the region of the allograft. L=liver, K=kidney, A=autologous heart, G=graft.
Figure 9:
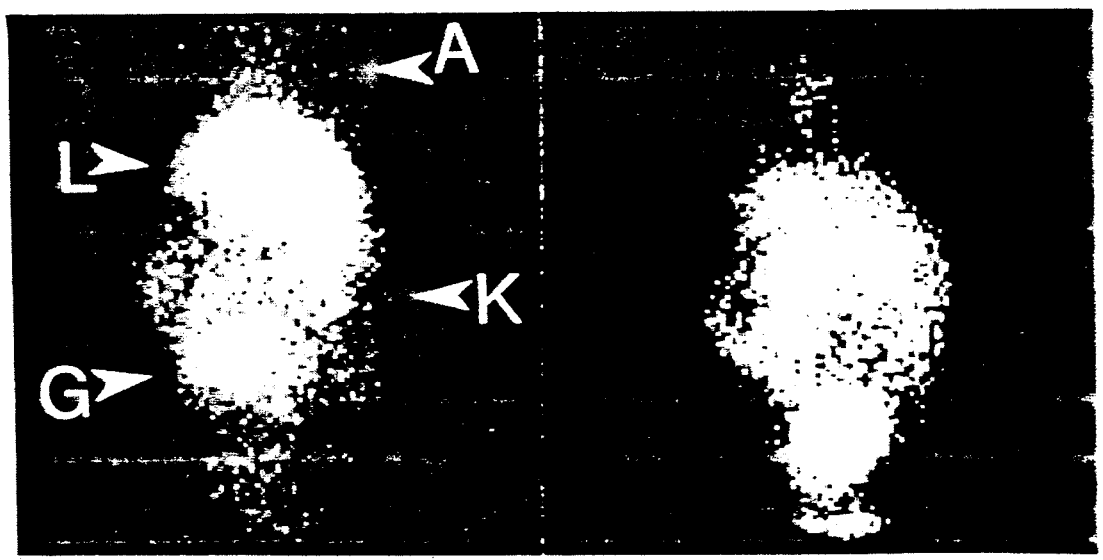
FIG. 9: Scintigrams of nontreated, allografted mice 10 days (left panel) and 14 days (right panel) after transplantation. The ratios of percent dose of antimyosin (% dose/g) of grafted heart to that of autologous heart are 7.4 and 10.7, respectively. Strong, unequivocal accumulation of antimyosin is visible in the regions of the allografts in both panels. L=liver, K=kidney, A=autologous heart, G=graft.
Figure 10:
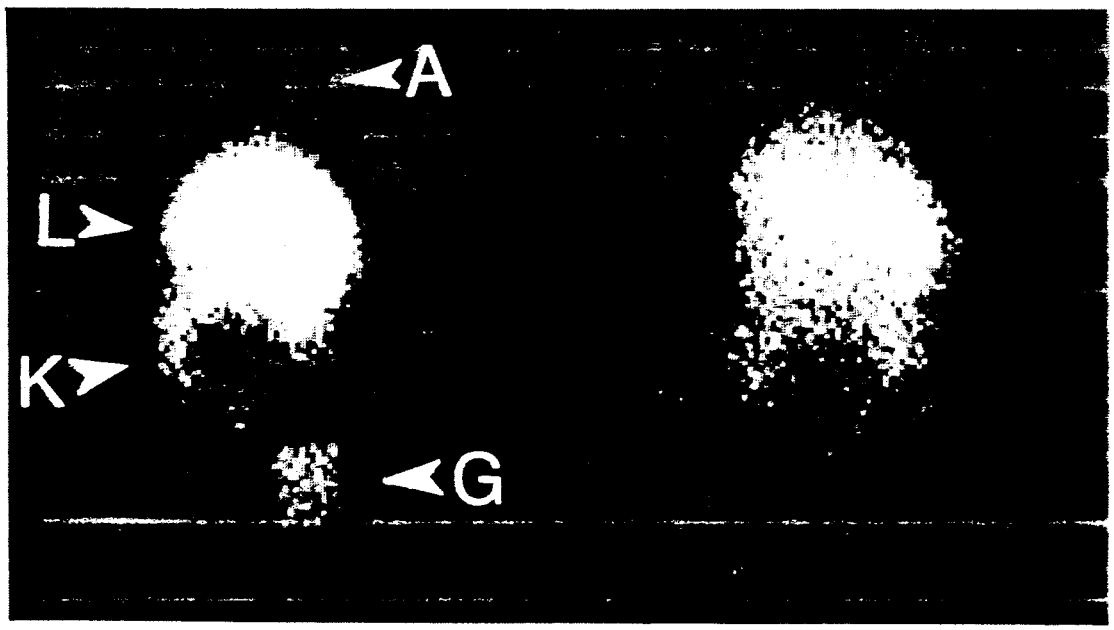
FIG. 10: Scintigrams of isografted mice 8 days (left panel) and 9 days (right panel) after transplantation. The ratios of percent dose of antimyosin (% dose/g) of grafted heart to that of autologous heart are 1.5 and 1.4, respectively. L=liver, K=kidney, A=autologous heart, G=graft.
Figure 11:
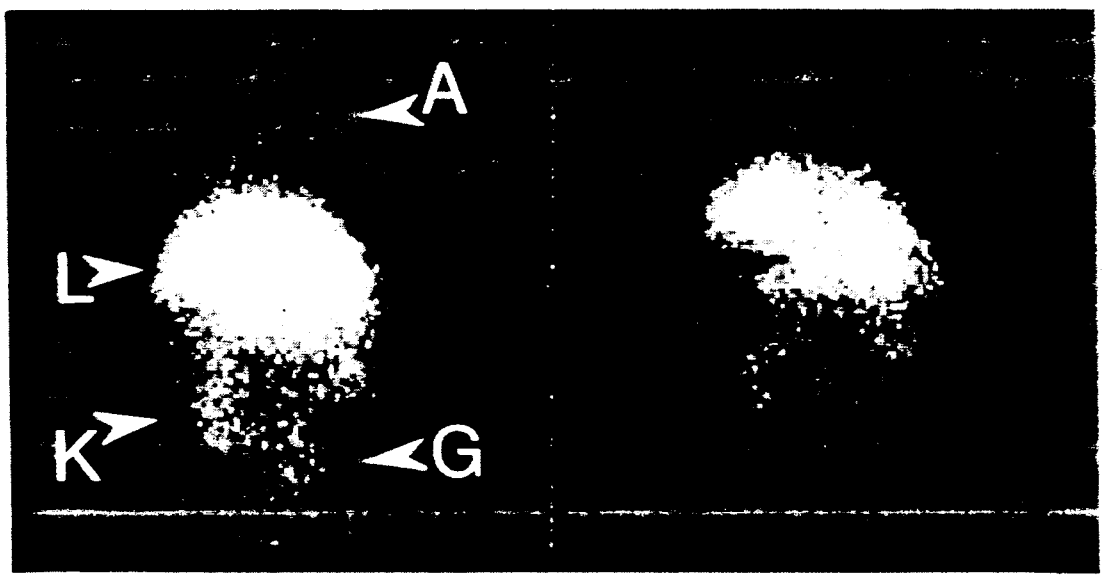
FIG. 11: Scintigrams of allografted mice treated with cyclosporine 14 days (left panel) and 10 days (right panel) after transplantation. Histological examinations showed severe rejection in the mouse shown in the right panel and nearly normal findings in the mouse shown in the left panel. The ratios of percent dose of antimyosin (% dose/g) of grafted heart to that of autologous heart are 7.2 (left panel) and 1.3 (right panel). L=liver, K=kidney, A=autologous heart, G=graft.

In all 9 isografted mice, in 16 of 19 allografted mice treated with cyclosporine, and in 16 of 30 nontreated, allografted mice the heart beat was normal (3+ to 4+) in the grafts at the time the animals were killed. The G/A in the 6 allografted mice that showed mildly impaired contraction (2+) (4.2±1.0) was greater than that in allografted mice with normal contraction (1.8±0.7) ($p<0.001$) (FIG. 6). The G/A was greater than 3.0 in 15 of 17 mice (88%) with a grade 1+ or 2+ heart beat and was less than 3.0 in 39 of 41 mice (95%) with a grade 3+ or 4+ heart beat regardless of the presence or absence of cyclosporine therapy. When allografted mice with normal contractility were divided into two groups according to the presence or absence of histological evidence of necrosis, the G/A in mice with no necrosis (1.5±0.5) was significantly lower than that in mice with necrosis (2.6±0.5) ($p<0.001$) (FIG. 7).

Scintigraphy

Antimyosin scans showed unequivocal accumulation of the tracer in allografts with high G/A ratios, relative to isografts or allografts with low G/A ratios. Representative images are shown in FIGS. 8 through 11. Allografted mice treated with cyclosporine without histological evidence of rejection showed no specific accumulation of radiolabeled antimyosin at any time after transplantation, whereas 3 mice with histological evidence of rejection as well as increased G/A ratios showed considerable uptake of radioactivity.

Biodistribution of Injected Antimyosin

The biodistribution of indium-111 antimyosin (% dose/g) in all organs was as follows: autologous heart (3.1±0.9%), liver (25.6±11.0), spleen (7.7±3.8), right kidney (17.1±7.9), right lung (3.8±2.5), bowel (3.4±1.4) and blood (3.0±4.6). There was no statistical difference in the dose/g of these organs among nontreated allografted, treated allografted, and isografted mice. The percent dose/g of grafted hearts is listed in Table 2.

DISCUSSION

This study demonstrates that an increase in uptake of indium-111 labeled antimyosin antibody accurately detects the existence of acute cardiac rejection. The degree of accumulation of indium-111 labeled antimyosin in rejected hearts also reflects the magnitude of rejection by histologic criteria. Antimyosin uptake precedes the decline in mechanical activity of the transplanted heart. Furthermore, the degree of uptake is not affected by cyclosporine therapy, but reflects the extent of myocyte necrosis due to rejection. These findings are reflected in the gamma scintigram.

The ability to detect cardiac allograft rejection noninvasively could play an important role in the management of patients who undergo heart transplantation. Rejection should be detectable before a decline in mechanical activity and the diagnosis should be sensitive, specific and effective even in the presence of immunosuppressive therapy with cyclosporine. Though several scintigraphic approaches for the diagnosis of rejection, such as technetium-99m pyrophosphate (McGregor, C. G. A., et al., *J. Nucl. Med.* 25:870-873 (1984)); thallium-201 (Pinedo, J. I., et al., *Eur. J. Nucl. Med.* 10:203-207 (1985); Barak, J. H., et al., *Transplant.* 45:687-692 (1988)), or indium-111 lymphocytes (Eisen, H. J., et al., *Circulation* 75:868-876 (1987); Rosenbloom, M., et al., *Transplantation* 46:341-346 (1988)), have been reported, none has proved clinically satisfactory (McKillop, J. H., et al., *Clin. Nucl. Med.* 6:375-377 (1981); ten Berge, R. J. M., et al., *J. Nucl. Med.* 24:615-620 (1983); Silberstein, E. B., et al., *J. Lab. Clin. Med.* 105:608-612 (1985)).

We previously showed that radiolabeled antimyosin antibody localizes in histochemically delineated regions of myocyte necrosis (Khaw, B. A., et al., *Circulation* 60:1527-1531 (1979)). Because myocardial necrosis is an obligatory component of rejection, it is reasonable to apply this method for detection of acute cardiac rejection.

In our study, we were able to demonstrate that ischemic necrosis did not occur if perfusion was interrupted for less than 60 minutes. By only including animals with shorter periods of ischemia, we were able to assess necrosis caused by transplant rejection alone. Prolonged storage of donor hearts in a cold solution has been shown to cause mechanical dysfunction (Blanchard, J. M., et al., *Microsurg.* 6:169-174 (1985)). Indeed, the results of our acute experiment using antimyosin clearly indicated that storage of donor hearts in a cold solution causes significant ischemic myocyte necrosis. Grafts with an ischemic time of more than 90 minutes showed significantly increased antimyosin uptake in comparison with grafts with an ischemia time of less than 60 minutes. It is, therefore, reasonable to exclude mice with an ischemic time of more than 60 minutes to minimize the effect of antimyosin uptake caused by intraoperative ischemic myocyte necrosis. The fact that isografts or non-rejected allografts showed no increase in antimyosin uptake as late as 15 days indicates that antibody uptake indeed correlates with rejection-associated myocyte necrosis. Thus, the potential for false positive scans caused by perioperative infarction could be excluded in our experiment.

As shown by Corry et al. (Corry, R. J., et al., *Transplant.* 16:343-350 (1973)), B10D2 mice rapidly reject hearts from B6AF1 mice. In their study of 7 mice with transplanted hearts, a sharp decline in impulse was observed between 7 and 22 days (median time of sharp decline, 11.5±1.1 days, SD) following surgery. In the present study, allografted mice were killed between 2 and 15 days after transplantation. Although some mice showed significant reduction in the intensity of cardiac impulse at the time of termination, none showed a complete absence of impulse.

Uptake of antimyosin (percent dose of indium-111 antimyosim/g grafted heart and G/A ratio) generally reflected the degree of rejection by histologic criteria. In nontreated cardiac allografts, antimyosin antibody accumulated progressively during the course of rejection. Antimyosin scintigraphy, reflecting the demonstrated antibody accumulation, proved to be a sensitive indicator of myocyte necrosis. The G/A was equal to or greater than 1.95 in 26 of 26 mice with necrosis, and was less than 1.95 in 29 of 32 mice without necrosis.

Mechanical dysfunction in the transplanted heart is the most serious outcome of cardiac rejection. However, the relation between deterioration in mechanical activity in allografts and uptake of labeled antimyosin has not been investigated previously. Antimyosin uptake is significantly increased in rejecting allografts with deteriorating mechanical activity compared with allografts with normal mechanical activity. We found that some mice with histological evidence of necrosis due to acute rejection showed apparently normal cardiac contractility. Even in these mice the G/A ratio was significantly greater than the ratios in mice with histologically normal grafts. This indicates that accumulation of antimyosin is a more sensitive early detector of rejection than is decline in mechanical activity.

Cyclosporine (15 mg/kg per day) suppressed rejection in the majority of allografted mice. As shown in FIG. 5, the G/A ratio remained low as late as 15 days after transplantation, with the exception of 3 mice. Histological examination revealed severe rejection in these 3 allografts. Scintigrams in these 3 animals showed significant accumulation of radioactivity in the allografts in comparison with cyclosporine-treated, allografted mice without histological evidence of necrosis. The absence of nonspecific positive scan or false negative scan during the period of cyclosporine administration attests to the usefulness of antimyosin scintigraphy during cyclosporine therapy. These results suggest that antimyosin scanning may be helpful in monitoring the effects of cyclosporine therapy clinically.

In conclusion, antimyosin scintigraphy can be used to detect cardiac rejection in its early stages, the efficiency of antimyosin scintigraphy is not affected by cyclosporine treatment, and antimyosin scintigraphy reflects the degree of severity of rejection by histologic assessment.

Although a variety of noninvasive techniques for the detection and quantitation of organ rejection have been explored, none has gained widespread use. Therefore, to date the diagnosis of rejection at an early stage usually requires frequent biopsy (Billingham, M. E., *Heart Transplant.* 1:25 (1981)). Because the biopsy procedure is invasive and subject to sampling errors, noninvasive and specific technique for diagnosing early rejection is

TABLE 1

| Histological grade n | Histological grade of rejection and Indium-111 antimyosin uptake | | | | |
|---|---|---|---|---|---|
| | Normal 11 | Mild 10 | Moderate | | Severe 17 |
| | | | necrosis (−) 12 | necrosis (+) 8 | |
| % injected dose/gram organ | 4.0 ± 1.9 | 5.2 ± 1.9 | 4.9 ± 1.9 | 8.5 ± 3.3$^a$ | 15.3 ± 9.2$^b$ |
| GA | 1.4 ± 0.4 | 1.5 ± 0.5 | 1.6 ± 0.5 | 2.6 ± 0.5$^c$ | 5.4 ± 2.5$^d$ |

G/A = the ratio of percentage injected dose of antimyosin of grafted heart to autologous heart.
$^a$ $p < 0.01$ versus normal or moderate without necrosis and $p < 0.05$ versus mild rejection.
$^b$ $p < 0.001$ verus normal, mild rejection or moderate rejection without necrosis and $p < 0.05$ versus moderate rejection with necrosis.
$^c$ $p < 0.001$ versus normal, mild or moderate without necrosis.
$^d$ $p < 0.001$ versus normal, mild, necrosis (−) or necrosis (+).

TABLE 2

| | Update of labeled antimyosin in transplanted hearts, autologous hearts and blood | | | | |
|---|---|---|---|---|---|
| | Number | | | | |
| | 9 | 8 | 11 | 11 | 19 |
| Grafted hearts (G) | 4.3 ± 1.7 | 7.2 ± 2.8 | 10.2 ± 5.8$^a$ | 15.6 ± 11.3$^a$ | 5.6 ± 3.3 |
| Autologous hearts (A) | 2.6 ± 0.8 | 3.3 ± 0.8 | 3.3 ± 0.9 | 2.7 ± 0.5 | 3.4 ± 0.9 |
| G/A | 1.7 ± 0.3 | 2.1 ± 0.6 | 3.3 ± 1.2$^b$ | 5.5 ± 3.1$^a$ | 1.8 ± 1.5 |
| Blood | 2.6 ± 4.6 | 3.5 ± 4.9 | 4.2 ± 5.1 | 3.0 ± 2.8 | 2.1 ± 4.4 |

Values are expressed by percent dose/gram of organ except for the G/A.
$^a$ $p < 0.01$ compared with isografted mice.
$^b$ $p < 0.001$ compared with isografted mice.

Example 2

The distribution of major histocompatibility complex (MHC) antigens in various organs and tissues has been well documented in animals and humans (Natali, P. G., et al., *Transplantation* 31:75 (1981); Koene, R. A. P., et al., *Kidney International* 30:1 (1986)). Normal, nucleated, nonlymphoid cells such as cardiac myocytes and nephrocytes express low levels of MHC class I antigens (MHC K and D in mice) and do not express detectable levels of NHC class 2 antigens (MHC IA and IE in mice). Recent immunohistological investigations, however, show that expression of class 2 antigens is enhanced in rejecting organs (Klein, J., et al., *Transplant Rev.* 30:82 (1976); Hall, B. M., et al., *Lancet* 1:247 (1984); Milton et al., *Transplantation* 4:499 (1986); Rose et al., *Transplantation* 41:776 (1986)), tissues undergoing autoimmune injury (Hanafusa, T., et al., *Lancet* 2:1111 (1983); Wuthrich, R. P., et al., *Am. J. Physiol.* 134:45 (1989)), viral disease (McMichael, A. J., et al., *Nature* 270:524 (1977)), and inflammatory states (Appleyard, S. T., et al., *Lancet* 1:361 (1985)). Because class 2 antigens are involved in antigen presentation on antigen presenting cells and play an essential role in inducing an immune response (Klein, J., et al., *Transplant Rev.* 305:82 (1976)), an alteration in MHC class 2 antigen expression is one of the initial immunological events of rejection and is thought to be an important part of the pathogenesis of rejection (Koene, R. A. P., *Transplant. Proc.* 21:602 (1989)).

desirable. It has been shown that detection of enhanced class 2 antigens is useful for diagnosing clinical rejection (Carlquist, J. F., et al., *Circulation* 80:II-672 (1989)). However, necessity of biopsied samples for immunohistological investigation limits the usefulness of this methodology. In this report, we demonstrate that increased expression of class 2 antigens in rejecting mouse hearts can be detected by isotope scintigraphy.

In the initial experiments, C3H/He mouse (All animals were purchased from Charles River Resources (Boston). All animal experiments were approved by Committee on Research Aninal Care Protocol Review Group and carried out under Massachusetts General Hospital and the NIH Guide for Care and Use of Laboratory Animals.) donor hearts were ectopically transplanted into Balb/c recipients. Recipient mice were randomly selected for scintigraphy within 3 to 7 days of transplantation. Our previous experience with this donor-recipient combination showed that rejection is complete 7 to 8 days after transplantation; thus, all allografts were beating at the time of scintigraphy.

Purified monoclonal antibodies specific for mouse IA and IE antigens (10-2-16 (Oi, V. T., et al., *Curr. Top. Microbiol. Immunol.* 81:115 (1978)) and 14-4-4S (Ozato, K., et al., *J. Immunol.* 124:533 (1980)), respectively) were labeled with $^{111}$indium and injected into recipient mice 24 hours before scintigraphy. Scintigrams of isografts (C3H/He hearts to C3H/He recipients or Balb/c hearts to Balb/c recipients) showed no significant increase in radioactivity in comparison with scintigrams of native hearts. We took this level of radioactivity to be background uptake in normal myocardium. In contrast, strong and unequivocal accumulation of labeled antibodies were apparent in scintigrams of rejecting allografts from the 4th day of operation.

For each scintigram, intensity of radioactivity at the graft region was obtained by setting an area of interest on the screen and compared with radioactivity of native heart. The ratio of radioactivity in the graft versus native heart increased progressively with time in allografts ($r=0.81$, $p<0.01$). Percent injected dose in excised grafts determined by gamma scintillation counting was $4.7\pm0.9$ (mean+SD) for grafts with normal histology ($n=6$), $6.9\pm2.1$ with mild rejection ($n=2$), $21.2\pm1.2$ with moderate rejection ($n=3$, $p<0.001$ vs. normal, and $p<0.05$ vs. mild), and $19.1\pm2.7$ with severe rejection ($n=3$)($p<0.001$ vs. normal).

The level of radioactivity reflected the histological severity of rejection. An allograft imaged on the fourth day after transplantation and another imaged on the fifth day showed moderate rejection with histological evidence of confluent cell infiltrates but without significant myocyte necrosis. These allografts showed significant increases in % injected dose of graft relative to that in isografts and non-rejecting allografts ($4.7\pm0.9$ vs. $22.4\pm0.07$, $p<0.001$) and could be scintigraphically identified.

As is shown by Milton et al. (Milton, A. D., et al., *J. Exp. Med.* 161:98 (1985)), myocytes in rejecting allografts were stained with anti-IA antibodies. Immunoperoxidase staining of an allograft was demonstrated. This observation was significantly different from that obtained from isografts or allografts treated with cyclosporine, in which no specific staining was observed. Although we did not perform quantitative analysis of class 2 expression in these grafts, the expression increased with the time after transplantation in non-treated allografts as expected from previous reports (Milton, A. D., et al., *J. Exp. Med.* 161:98 (1985)).

Cyclosporine is an immunosuppressive drug that inhibits lymphokine production by helper T cells in vitro and has been widely used to alleviate tissue allograft rejection in vivo (Shevach, E. M., *Ann. Rev. Immunol.* 3:397 (1985)). It has also shown that cyclosporine suppresses induction of MHC class 2 antigens in spite of the fact that cyclosporine-treated grafts show substantial infiltrates (Milton, A. D., et al., *Transplantation* 42:337 (1986)). This is almost certainly a consequence of the suppressed release of interferons, particularly, interferon-gamma, from the infiltrating leukocytes by this drug (Abb, J., et al., *Transplant. Proc.* 15:2380 (1983)). As is expected from these observations, cyclosporine-treated allografts did not show any increase in radioactivity relative to isografts even after 7 days of transplantation in our scintigraphic study.

We also analyzed the source of antibody uptake in rejecting allografts in different donor-recipient combinations (Table 3). To rule out the possibility that infiltrating leukocytes provide class 2 antigens that could bind to injected labeled antibodies, Balb/c mouse (H2$^d$) hearts were transplanted into C3H/He (H2$^k$) recipients and scintigraphy was performed with the 10-2-16 antibody, which binds IA$^{k,r,s,f}$ but not with IA$^d$. Even though the allograft showed histological evidence of severe rejection 10 days after transplantation, there was no increase in the radioactivity in the graft relative to nonrejecting allografts. In another experiment, Balb/c donor hearts were transplanted into C57BL/6 (H2$^b$, IE$^-$) recipients. After 6 to 10 days, the mice were injected with radiolabeled 10-2-16 or 14-4-45 (IE$^{k,d,p,r}$). Rejecting Balb/c allografts in C57BL/6 mice were visualised with 14-4-45 antibody but not with 10-2-16 antibody (Table 3). These data show that class 2 antigens from donor myocytes are solely responsible for the positive scintigram of rejecting allografts. Also, the possibility that nonspecific accumulation of immunoglobulin was the source of antibody accumulation can be ruled out.

Our data suggest that cardiac rejection can be detected by anticlass 2 scintigraphy at a stage with lymphocyte infiltration but without significant myocyte necrosis. This method is useful for distinguishing active cellular infiltrates which are the first sign of a rejection episode from innocuous and self-limiting infiltrates frequently seen with cyclosporine.

Although it should be noted that class 2 antigens induction is likely to occur whenever active inflammation involving T lymphocytes from whatever cause is present, this scintigraphic detection of induced class 2 antigens is potentially useful not only for non-invasive early diagnosis of rejection of other organs such as kidney, liver and pancreas but also for detection or localization of autoimuune disease which is shown to express an enhancement of class 2 antigens in the affected organs (Hanafusa, T., et al., *Lancet* 2:1111 (1983); Wuthrich, R. P., et al., *Am. J. Physiol.* 134:45 (1989)). Furthermore, since changes in class 2 expression is supposed to regulate the immune response, serial scintigraphic detection of changes in class 2 expression may allow us to investigate the immunological role of class 2 expression in the development of rejection and other immunological disorders.

TABLE 3

| ID | Donor | Recipient | Days Post-transplant | Histology | Antibodies | Graft/Native heart (% ID) | Scintigram |
|---|---|---|---|---|---|---|---|
| C16 | CH3 | Balb/c | 6 | Severe | 10-2-16 + 14-4-4S | 19.5 | Positive |
| C32 | Balb/c | C3H | 10 | Severe | 10-2-16 | 1.6 | Negative |
| C35 | Balb/c | C57BL/6 | 8 | Severe | 10-2-16 | 3.1 | Negative |
| C36 | Balb/c | C57BL/6 | 7 | Severe | 14-4-4S | 10.4 | Positive |

Effects on different donor-recipient combination and different antibody specificity on labeled anti-class 2 accumulation in rejecting allografts not shown. All allografts showed histological evidence of severe rejection. 10-2-16 antibody (IA$^{k,r,s,f}$) binds with C3H (H2$^k$) class 2 antigens but not with Balb/c (H2$^d$) and C57BL/6 H2$^b$, IE$^-$) mice class 2 antigens. 14-4-4S antibody (IE$^{k,d,p,r}$) binds with C3H and Balb/c mice class 2 antigens but not with C57BL/6 mice class 2 antigens. The fact that C32 and C35 showed negative scan and C36 showed positive scan indicates accumulation of labeled antibodies in rejecting allografts is not due to nonspecific binding of immunoglobulin nor of class 2 antigens on infiltrating recipient's lymphocytes but is due to induced class 2 antigens on donor heart myocytes. %

ID=percent injected dose per gram of graft (Ozata et al., *J. Immunol.* 124:533 (1980)).

EXAMPLE 3

Animals

Male, inbred Balb/c ($H2^d$) and C3H/He ($H2^k$) mice were obtained from the Charles River Breeding Laboratory (Boston, Mass.). C57BL/6 ($H2^b$, IE−) male mice were purchased from Jackson Laboratory (Bar Harbor, Me.). All animal experiments were approved by the Committee on Research Animal Care Protocol Review Group and carried out according to Massachusetts General Hospital guidelines and the NIH Guide for Care and Use of Laboratory Animals.

Scintigraphy

Hybridoma cell lines, 10-2-16 (anti-mouse $[A^{k,r,s,f}]$)[24] and 14-4-4S (anti-mouse $IE^{1k,d,p,r}$)[25] were obtained from ATCC (Rockville, Md.). The specificity and affinity of the monoclonal antibodies have been described. Hybridoma cells were grown in DMEM medium supplemented with 10% fetal calf serum and 0.1% gentamicin, and monoclonal immunoglobulins were purified by Protein A affinity chromatography (Pharmacia, N.J.). Monoclonal antibodies 10-2-16 and 14=4=4S were labeled with $^{111}$indium by using a bifunctional chelating agent(diethylenetriaminepentaacetic acid (DITPA))[26-28]. Approximately 100 uCi of $^{111}$indium-DTPA-antibody (10-2-16, 14=4=4S, or both) was injected into the vein of the recipient mouse 24 hours before scintigraphy. Scintigraphy was performed with a gamma camera (Ohio Nuclear 100) equipped with a 3-mm pinhole collimator as described. Both energy peaks (173 and 247 Kev) of $^{111}$indium were used for count acquisition. For each scintigram, the intensity of radioactivity in the graft was measured in comparison with that in the native heart after an area of interest had been set by computer planimetry.

Tissue Analysis

Mice were killed after scintigraphy. Venous blood was withdrawn and the autologous heart, transplant heart, liver, spleen, kidneys, lungs were excised. Both hearts were washed thoroughly with saline. The biodistribution of radioactivity was determined as described. The ratio of percent injected dose per gram of grafted heart to that of autologous heart was determined for each mouse.

Organ Grafting and Animal Groups

Heterotopic mice cardiac transplantation was performed by the microvascular technique described before. In 12 mice, C3H/He hearts were transplanted into Balb/c recipient mice. Two of them were treated with cyclosporine (15 mg/kg/day, s.c. injection). Two mice were isografted (Balb/c heart into Balb/c recipient and C3H heart into C3H recipient). Mice were randomly chosen for scintigraphy from 3 to 7 days of transplantation, and labeled 10-2-16 and 14-4-4S antibodies were injected.

In our second set of experiments, we analyzed radiolabeled antibody uptake in rejecting allografts in various donor-recipient combinations (Table 2). A Balb/c mouse heart was transplanted into C3H/He mouse and injected with $^{111}$indium-labeled 10-2-16 antibody. A C3H/He heart was transplanted into a Balb/c mouse and injected with $^{111}$indium-labeled 14-4-4S antibody. Two Balb/c mouse hearts were transplanted into C57BL/6 mice. One mouse was injected with labeled 10-2-16 antibody and the other was injected with labeled 14-4-4S. In this experiment cardiac graft contractility was assessed daily by direct palpation. Scintigraphy was performed right after the confirmation of a significant decline of graft beat in these mice.

Histological Examination

Grafted and autologous hearts were embedded in paraffin and stained with hematoxylin and eosin. The samples were submitted for blinded histopathologic evaluation by two examiners and were classified into four groups according to the criteria by Billingham as follows: normal, mild rejection, moderate rejection, and severe rejection.

Immunoperoxidase Staining

Cardiac allografts were frozen in nitrogen immediately after harvesting, and cryostat section (4 um) were cut, air-dried on gelatinized slides, and stored at −20° C. After thawing, the sections were coated with 10% horse serum and allowed to incubate for 60 minutes (all incubations were at room temperature). They were then incubated for 60 minutes with purified biotinylated 10-2-16 antibody at saturating concentrations. This step was followed by 60 minutes incubation with the avidin-biotin-horseradish peroxidase complex (Vecter). Peroxidase activity was detected after a 5-min incubation with 3,3' diaminobenzidine 0.5 mg.ml) containing 0.015% $H_2O_2$.

Statistical Analysis

A $p>0.05$ was considered nonsignificant in comparisons between multiple groups of data. All data were expressed at the mean ±standard deviation. Linear regression was computed by the least squares method.

RESULTS

Histopathology And Radiotracer Uptake

A broad spectrum of histological findings was present, ranging from nearly normal to severe rejection. Labeled antibody uptake and histopathological data are listed in Table 4. The ratio of radioactivity by tissue counting in the grafted versus native heart in two isografted mice was 1.9 and 2.6. Because this slight increase in radioactivity in isografts was also observed after injection of radiolabeled mouse immunoglobulin of irrelevant specificity, we conclude that myocyte necrosis of nonspecific inflammation caused by operatic manipulation was responsible for the increase in radioactivity.

Figure 12:
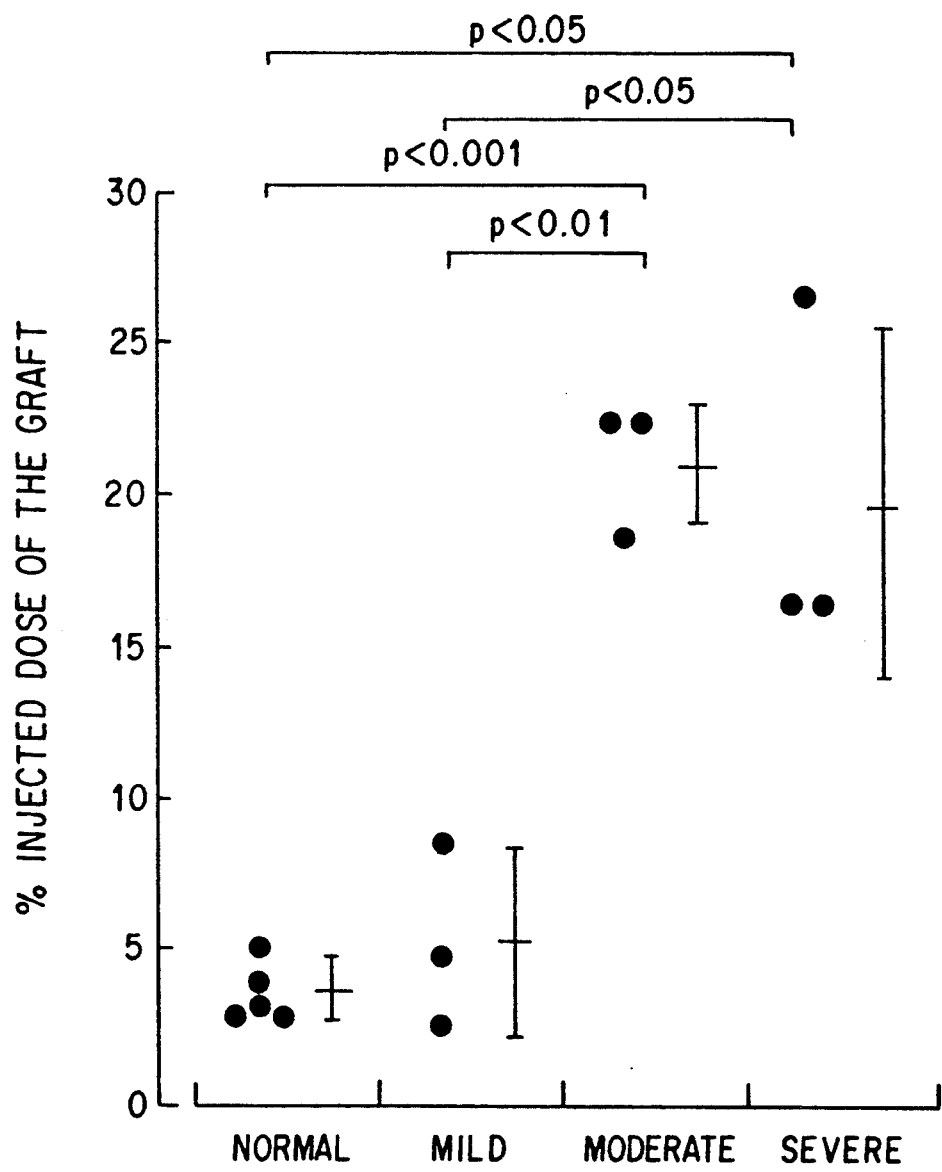
FIG. 12. Percent injected dose of anti-MHC class II antibody per gram of grafted heart compared with histological degree of rejection. The % injected dose/g in mice that showed moderate rejection and severe rejection is significantly greater than the % dose/g in normal and mild rejection.
Figure 13:
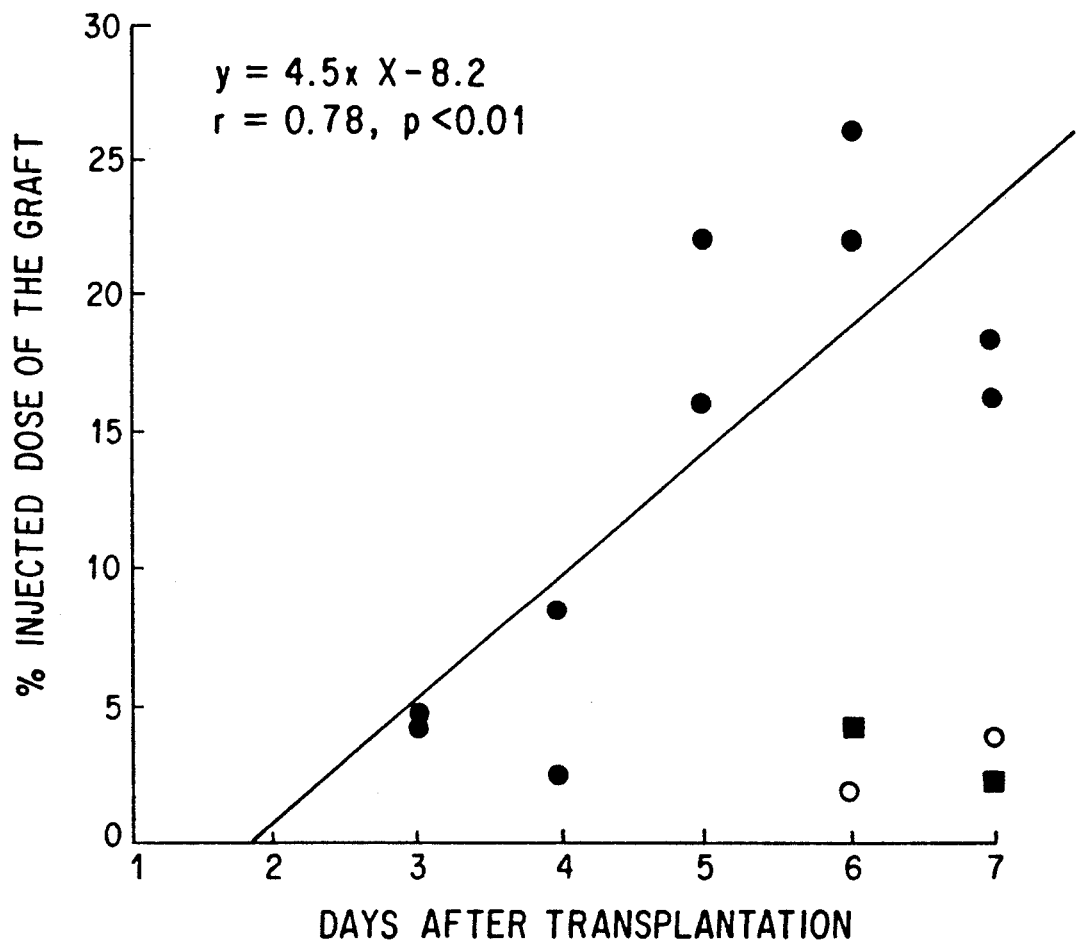
FIG. 13: Time course of $^{111}$indium-anti-MHC class II antigen antibody uptake (% dose/g) in grafted hearts. Localization is expressed as the percent injected dose per gram of wet tissue. The percent injected dose/gram in nontreated allografts (filled circles, C3H/He heart in Balb/c recipient) increased progressively with time, whereas that in isografts (filled squares, Balb/c heart in Balb/c recipient or C3H/He heart in C3H/He recipient) or in cyclosporine-treated allografts (open circles, C3H heart in Balb/c recipient) remained low.

Regardless of the time after transplantation and the presence or absence of cyclosporine therapy, the level of radiotracer uptake on reflected histological measurements of the severity of rejection. The percent injected dose in excised grafts was 3.7±1.0 for normal grafts (n=5), 5.4±3.1 for grafts with mild rejection (n=3), 21.2±2.1 for grafts with moderate rejection (n=3, $p<0.001$ versus normal, $p<0.01$ versus mild), and 19.8±5.8 for grafts with severe rejection (n=3, $p<0.05$ versus normal and mild) (FIG. 12). The percent injected dose of excised grafts increased progressively with time in allografts (percent injected dose in grafts=4.5×days−8.2, r=0.78, $p<0.01$, n=10) (FIG. 13). The ratio of radioactivity in the graft versus autologous heart also increased progressively with time (G/A=3.5×days−7.6, r=0.74, $p<0.05$, n=10). Radiolabeled antibody uptake in cyclosporine-treated allografts, for which there was no histological evidence of rejection, did not increase relative to that in isografts even seven days after transplantation.

Scintigraphy

Figure 14:
FIG. 14: Scintigrams showing temporal progression of $^{111}$indium-anti-MHC class II antigen antibody uptake in C3H/He hearts engrafted in Balb/c recipient mice. Labeled antibodies (10-2-16 and 14-4-4S) were injected in the recipient mice 24 hours before scintigraphy. (A) An allografted mouse three days after transplantation. The graft with no evidence of histopathological rejection is not visualized. S=spleen. (B) An allografted mouse four days after transplantation. An uptake in the mildly rejected graft is obscure. (C) Five days after transplantation. Histopathological examination showed moderate rejection in this graft. An unequivocal, strong uptake of radiotracer is observed in the graft. L=liver, K=kidney, B=bladder, G=graft. (C) and (D) show grafts six days and seven days, respectively, after transplantation. Both grafts revealed severe rejection by the histological examination and could be identified by the scintigrams. (F) An allografted mouse treated with cyclosporine. Seven days after transplantation. The graft, which revealed no rejection by the histopathological examination, could not be identified.

The magnitude of radioactivity measured by tissue counting were reflected in scintigrams. A good correlation was observed between the ratio of graft to native heart radioactivity measured by tissue counting and the ratio measured by computer planimetry from the scintigrams ($P=0.29\times G/A+1.6$, $r-0.86$, $n=14$, $p<0.001$, where P—ratio of radioactivity in the graft versus autologous heart measured by computer planimetry). Correlation between the intensity of radiotracer signal from the scintigram and the percent injected dose (% ID) in graft was also good ($P=0.24\times\%$ $ID+1.1$, $r=0.90$, $n=10$, $p<0.001$). Strong and unequivocal accumulation of labeled antibodies was apparent in scintigrams of rejecting allografts from the 4th day of transplantation (FIG. 14). In contrast to mice with rejecting allografts, isografted mice and cyclosporine-treated mice showed no specific accumulation of radiolabeled antibodies 6 and 7 days after transplantation.

In allografted mouse imaged on the fourth day of transplantation (mouse #3, Table 4) and another imaged on the fifth day (mouse #6), the tissue counting and scintigram revealed strong uptake of radiotracer whereas the histological studies showed evidence of cell infiltrates but no significant myocyte necrosis.

Antigen Source Study

In the C3H/He (H2$^k$) donor, Balb,c (H2$^d$) recipient combination the rejecting graft was clearly visualized by radiolabeled 14=4=4S antibody (anti-IE$^{k,d,p,r}$). On the contrary, in the Balb/c donor, C3H/He combination there was no increase in radiolabeled 10-2-16 (anti-IA$^{k,r,s,f}$) antibody uptake in the rejecting allograft relative to nonrejecting allografts, even though the graft showed histological evidence of severe rejection 10 days after transplantation. And Balb/c donor, C57BL/6 (H2$^b$), IE$^{1-}$) recipient combination, in which one mouse was injected with radiolabeled 10-2-16 8 days after transplantation and another with radiolabeled 14-4-4S 7 days after transplantation, rejecting allografts with H2$^d$ antigens in mice with H2$^b$ antigens were visualized by an anti-IE$^{k,d,p,r}$ antibody but not by an anti-IA$^{k,r,s,f}$ antibody (Table 5).

Immunoperoxidase Staining

Figure 15:
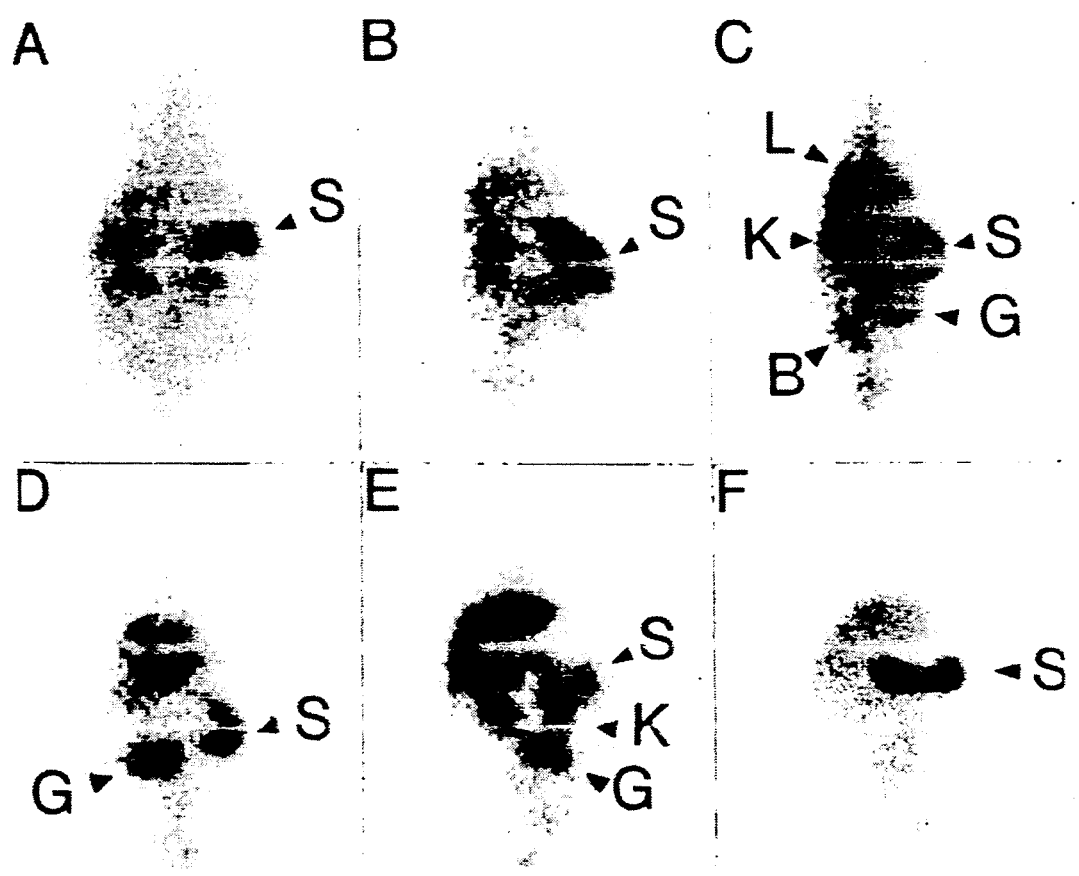
FIG. 15. Cardiac grafts stained by immunoperoxidase method. Tissue samples were stained by anti-IA$^k$ (10-2-16) antibody. (A): Isografted C3H/He heart. Six days after transplantation. (B) C3H/He cardiac allograft transplanted into Balb/c recipient. Five days after transplantation. H-E staining revealed moderate rejection in this allograft.
Figure 16:
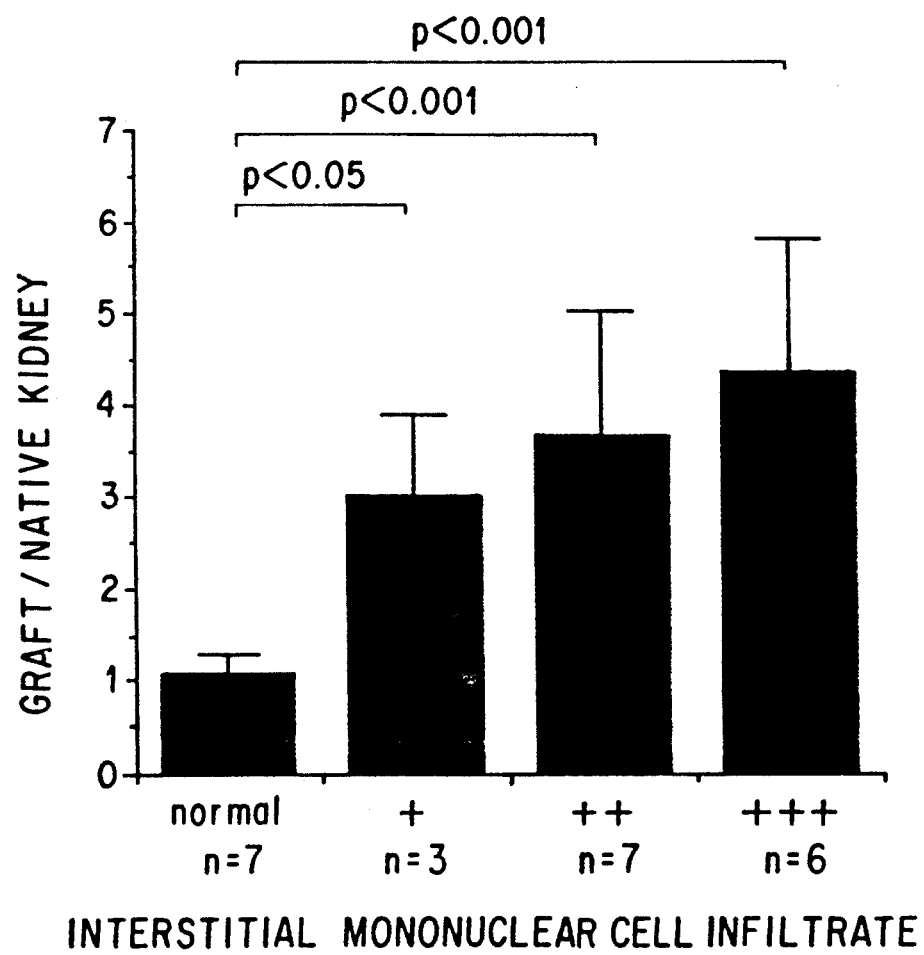
FIG. 16. Interstitial mononuclear cell infiltrate.
Figure 17:
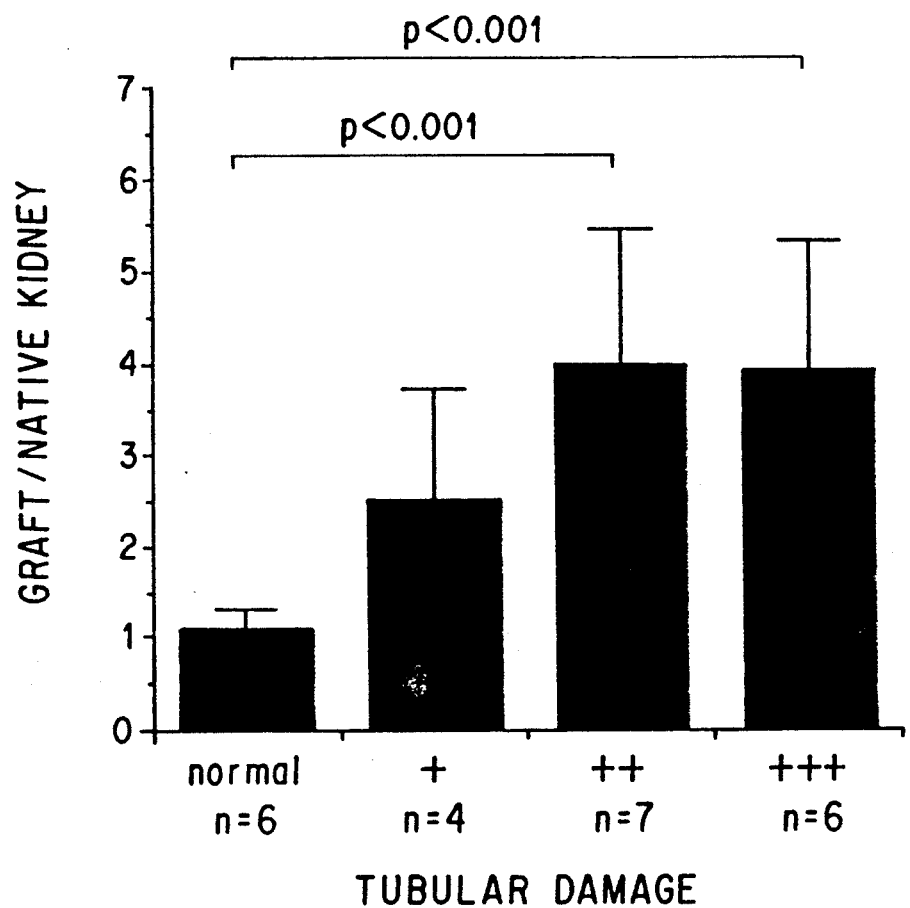
FIG. 17. Tubular damage is shown.
Figure 18:
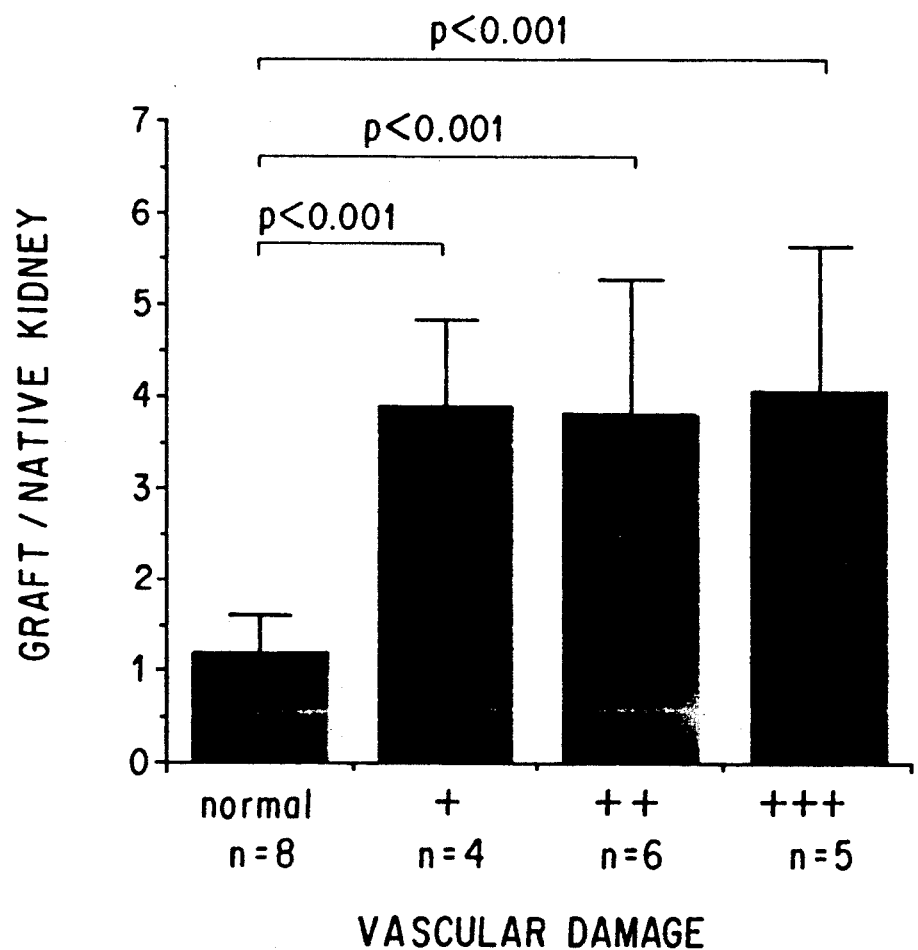
FIG. 18. Vascular damage is shown.
Figure 19:
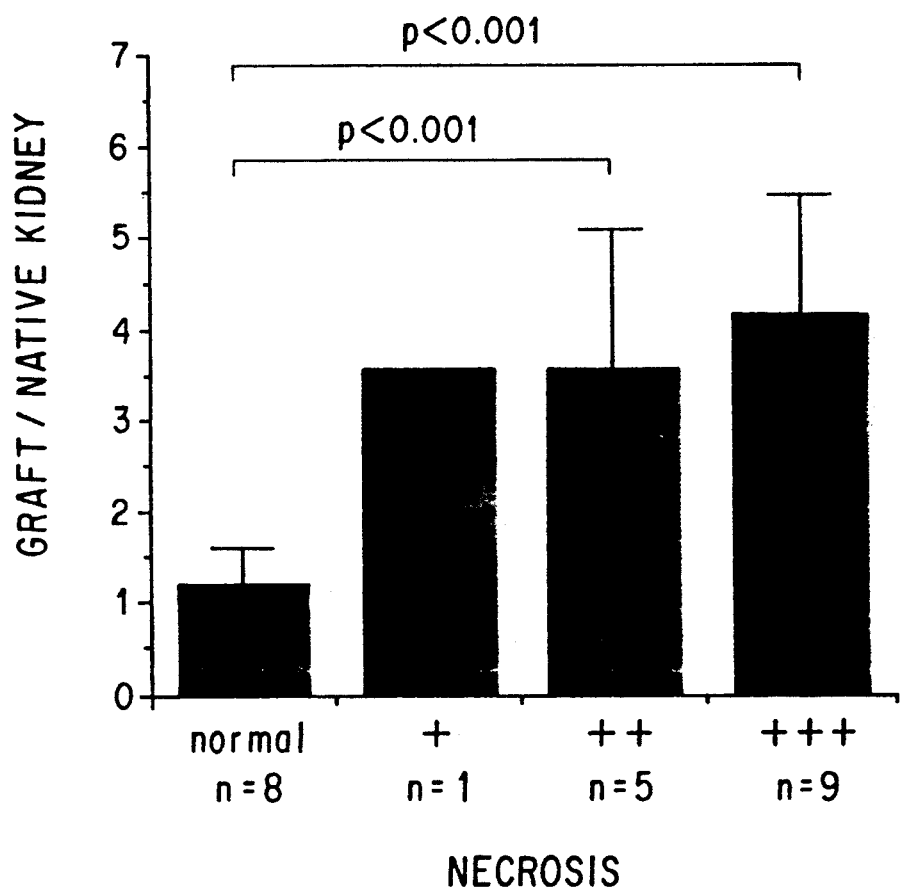
FIG. 19.
Figure 20:
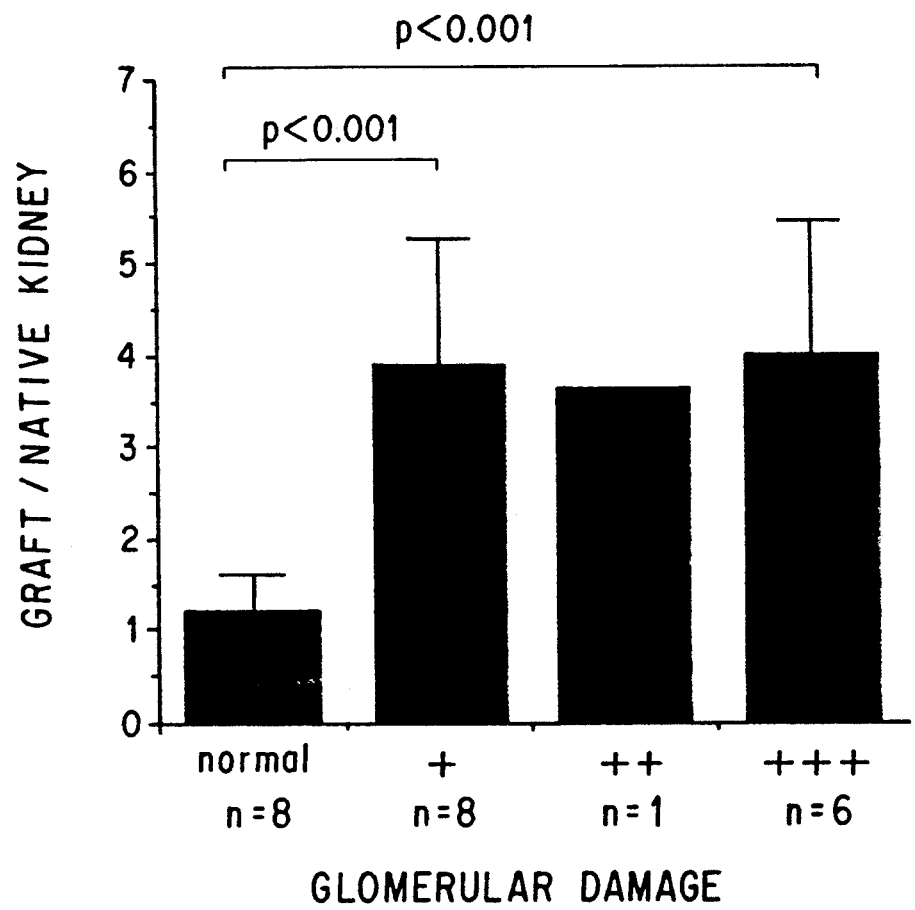
FIG. 20. Glomerular damage is depicted in FIG. 20.

Anti-IA$^k$ antibody 10-2-16 stained myocytes in rejecting allografts (FIG. 15). These findings were significantly different from that obtained with isografts or allografts treated with cyclosporine, in which there was no specific staining. Although we did not quantitatively analyze class II antigen expression in these grafts, antigen expression apparently increased with time after transplantation in nontreated allografts.

DISCUSSION

The results of this study demonstrate that anti-MHC class II antibody scintigraphy detects cardiac rejection. The scintigraphy was sensitive in detecting early rejection before the development of significant myocyte necrosis. The results also clearly show that induced MHC class II antigens on donor cardiac myocytes are the unique antigen source for the positive scan in the rejecting heart.

Although a variety of noninvasive techniques for detection and quantification of rejection have been explored, none has gained widespread use. Antimyosin scintigraphy is a potentially useful method for diagnosing cardiac rejection in the clinical setting, because myocyte necrosis is a direct result of the rejection and is usually regarded as an indication for additional therapy for rejection. However, it is also true that myocyte necrosis is not a specific phenomenon for rejection and that is relatively an advanced sign of cardiac rejection. Therefore, more sensitive and specific scintigraphic detection for cardiac rejection would be practically useful.

MHC class I and class II molecules, known as transplantation antigens, play an essential role in the pathogenesis of rejection (Koene et al., *Kidney International* 30:1-8 (1986); Koene, R. A. P., *Transplant Proc.* 21:602-604 (1989)). Although low levels of class I antigens are expressed in the normal cardiac myocytes (Daar et al., *Transplantation* 38:287-298 (1984)), class II antigens are not detected (Natali et al., *Transplantation* 31:75-78 (1981); Klein et al., *Transplant Rev.* 30:83-100 (1980)). However, induction of both class I and class II antigens is reported in rejecting kidney (Koene et al., *Kidney International* 30:1-8 (1986); Hall et al., *Lancet* 1:247-251 (1984): Benson et al., *J. Immunol.* 134:7-9 (1985)), heart (Milton et al., *J. Exp. Med.* 161:98-112 (1985); Rose et al., *Transplantation* 41:776-780 (1986); Ahmed-Ansari et al., *Transplantation* 45:972-978 (1988); Sell et al., *J. Heart Transplant* 7:407-418 (1988); Carlquist et al., *Transplantation* 50:582-588 (1990)), liver (Settaf et al., *Transplantation* 46:32-40 (1988)) and pancreas (Steiniger et al., *Transplantation* 40:234-239 (1985)) allografts. Milton et al. (Milton et al., *J. Exp. Med.* 161:98-112 (1985); Milton et al., *Transplantation* 41:499-508 (1986)) showed the massive induction of donor-type class II antigens in rejecting rat cardiac allografts. In the series of six patients with cardiac transplantation reported by Sell et al. (Sell et al., *J. Heart Transplant* 7:407-418 (1988)) an increase in the level of MHC class II antigen expression occurred always before histologic evidence of moderate rejection. All patients showed a decrease in the expression of class II antigens after the episodes of rejection. It is, therefore, reasonable to use the induced donor-type class II antigens on the allografted heart as targets of imaging in the detection of early cardiac rejection.

In our series of C3H/He donor, Balb/c recipient combination, we used both anti-IA and anti-IE antigens which react with both donor and recipient antigens. In contrast to nonrejecting allografts and isografts, which were not visualized, allografts with histological evidence of rejection were clearly identified by the scintigraphy. Radiolabeled antibody uptake in rejecting allografts increased progressively with time in proportion to the severity of rejection. Although all allografts were beating at the time of sacrifice, two allografts killed on the 7th day showed obvious reduction in the graft beat detected by direct palpation. The significant loss of myocytes in these mice may account for the reduction of radiotracer uptake observed on the seventh day.

It is of interest that anti-class II antibody uptake was dissociated from myocyte necrosis. In an allografted mouse imaged on the fourth day after transplantation and another imaged on the fifth day, the scintigrams revealed strong uptake of radiotracer whereas the histological studies showed evidence of cell infiltrates but no significant myocyte necrosis. There was significant increase in percent injected dose in these grafts relative to that in isografts and nonrejecting allografts.

Cyclosporine inhibits lymphokine production by helper T cells in vitro and is widely used to alleviate tissue allograft rejection in vivo (Shevach, E. M., *Ann. Rev. Immunol.* 3:397–423 (1985)). Cyclosporine also suppresses induction of MHC class II antigen, in spite of the fact that cyclosporine-treated grafts show evidence of substantial leukocyte infiltration (Milton et al., *Transplantation* 42:337–347 (1986)). This suppression of MHC antigen induction is almost certainly a consequence of the suppressed release of interferon-gamma from the infiltrating leukocytes (Abb et al., *Transplant. Proc.* 15:2380–2382 (1983); Skoskiewicz et al., *J. Exp. Med.* 162:1645–1664 (1985)). Not surprisingly, in our scintigraphic study radiolabeled antibody uptake in cyclosporine-treated allografts, for which there was no histological evidence of rejection, did not increase relative to that in isografts even after 7 days of transplantation.

Immunoperoxidase staining of the rejecting allografts and scintigraphic studies using various donor-recipient combinations with two antibodies of different specificity show that induced class II antigens on donor myocytes are solely responsible for antibody uptake in the positive scintigrams of rejecting allografts. We observed increasing staining intensity of class II IA antigen on the myocytes from rejecting allografts. These findings were significantly different from that obtained with isografts, nonrejecting allografts or cyclosporine-treated allografts.

As shown in the Table 5, rejecting allografts were imaged only by anti-class II antibody reacts with donor antigen. The strong uptake of antibody in the recipient's spleen indicates the reactivity of the antibody with recipient's class II antigens, because normal lymphocytes, especially B cells, express class II antigens. Regardless of the positive and negative scan of the recipients' spleen or the strain of recipients, the rejecting Balb/c (H2$^d$) grafts were visualized only by 14-4-4S (anti-IE$^{k,d,p,r}$) but not by 10-2-16 (anti-IA$^{k,r,s,f}$) antibody. These results also out the possibility of nonspecific accumulation of antibody (immunoglobulin) in the site rejection.

This study demonstrates that cardiac rejection can be detected by anti-class II antibody scintigraphy at the stage at which there is leukocyte infiltration but no significant myocyte necrosis. This method may be particularly useful for distinguishing the active cellular infiltrates that are the first sign of a rejection episode from the innocuous and self-limiting infiltrates frequently seen with cyclosporine. Since the level of HLA-DR antigen on rejecting cardiac cells decreases after intensive immunosuppressive therapy (Sell et al., *J. Heart Transplant* 7:407–418 (1988)), MHC class II antigen scintigraphy may simplify the follow up of patients with episodes of rejection.

Enhancement of class II antigen expression in rejecting allografts is reported not only in the heart but also in other organs. Because of the low expression of class II antigen in the normal kidney (Koene et al., *Kidney International* 30:1–8 (1986); Hall et al., *Lancet* 1:247–251 (1984)) and pancreas (Steiniger et al., *Transplantation* 40:234–239 (1985)) rejection of these organs can be imaged by the MHC class II scintigraphy.

TABLE 4

Donor-recipient combination, immunosuppression, days after transplantation, anti-MHC class II antibody uptake, and histological degree of rejection.

| Mouse | Donor | Recipient | Cyclosporine (15 mg/kg/day) | Days after transplant | #ID | Graft/native heart tissue counting | Graft/native heart scintigram | Histological degree of rejection |
|---|---|---|---|---|---|---|---|---|
| 1 | C3H/He | Balb/c | — | 3 | 4.19 | 1.7 | 1.4 | normal |
| 2 | C3H/He | Balb/c | — | 3 | 4.82 | 2.0 | 2.2 | mild |
| 3 | C3H/He | Balb/c | — | 4 | 8.84 | 3.3 | 2.0 | mild |
| 4 | C3H/He | Balb/c | — | 4 | 2.63 | 3.4 | 3.3 | mild |
| 5 | C3H/He | Balb/c | — | 5 | 16.26 | 10.6 | 4.5 | severe |
| 6 | C3H/He | Balb/c | — | 5 | 22.32 | 20.1 | 4.5 | moderate |
| 7 | C3H/He | Balb/c | — | 6 | 22.40 | 11.3 | 7.1 | moderate |
| 8 | C3H/He | Balb/c | — | 6 | 26.46 | 20.0 | 8.6 | severe |
| 9 | C3H/He | Balb/c | — | 7 | 18.79 | 14.3 | 6.5 | moderate |
| 10 | C3H/He | Balb/c | — | 7 | 16.50 | 12.2 | 5.7 | severe |
| 11 | C3H/He | Balb/c | + | 6 | 3.38 | 1.4 | 2.2 | normal |
| 12 | C3H/He | Balb/c | + | 7 | 2.95 | 2.5 | 2.0 | normal |
| 13 | C3H/He | C3H/He | — | 6 | 5.29 | 2.6 | 1.4 | normal |
| 14 | Balb/c | Balb/c | — | 7 | 2.91 | 1.9 | 2.5 | normal |

TABLE 5

Uptake of $^{111}$In-labeled anti-class II antibodies 10-2-16 and 14-4-4S in rejecting mouse heart allografts in various donor-recipient combination.

| Mouse # | Donor | Recipient | Days after transplant | Histological degree of rejection | Antibody | Graft/native heart (% ID)* | Scintigram Graft | Scintigram Spleen |
|---|---|---|---|---|---|---|---|---|
| 15 | C3H/He | Balb/c | 6 | severe | 14-4-4S | 19.5 | + | + |
| 16 | Balb/c | C3H/He | 10 | severe | 10-2-16 | 1.6 | — | + |
| 17 | Balb/c | C57BL/6 | 8 | severe | 10-2-16 | 3.1 | — | — |
| 18 | Balb/c | C57BL/6 | 7 | severe | 14-4-4S | 10.4 | + | — |

*percent injected dose/g organ.

Example 4

Renal allograft rejection is diagnosed largely on the basis of renal function test indicating graft damage associated with rejection. However, these are not entirely diagnostic for immune rejection and do not necessarily reflect early changes caused by rejection. The definitive standard therefore remains histological examination of tissue taken from the graft. However, because of invasiveness, subjectiveness of the interpretation, sampling errors inherent to the biopsy procedure, noninvasive and sensitive method of diagnosis of early rejection is desired. Although many less invasive blood tests have been proposed, none has gained wide-spread use to date.

Hall et al., (Hall et al., Lancet 1:247-251 (1984)) reported that expression of HLA-DR antigens is increased on renal tubular cells in renal transplants in humans. Russell and co-workers revealed that major histocompatibility complex class II antigens are induced in murine renal transplant (Benson et al., J. Immunol. 134:7-9 (1985)). Since normal, nucleated nonlymphoid cells express low levels of class I antigens and do not express detectable levels of MHC class II antigens, class II antigens induced on the rejecting nephrocytes are possible indicator of rejection. We have already shown that rejecting mouse and rat cardiac allografts can be visualized before the advent of myocyte necrosis by a radioimmune scintigraphy using $^{111}$indium labeled monoclonal antibodies which react with donor specific or nonspecific class II antigens. Here, a new scintigraphic technique to detect kidney allograft rejection is disclosed.

The details of the radio immunoscintigraphy using $^{123}$I Labeled anti-MHC class II (IE) monoclonal antibody in a mouse kidney allograft model. Effects of immunosuppressive treatment on the scintigram and relation to functional deterioration were also evaluated.

MATERIALS AND METHOD

Animals

Balb/c mice (H2$^d$) and C3H/He mice (H2$^k$) were purchased from Charles River Resources (Boston, Ma.). All animal experiments were approved by the Committee on Research Animal Care Protocol Review Group and carried out according to Massachusetts General Hospital guidelines.

Antibodies

Hybridoma cell line designated as Y17 (anti-IE$^{b,k,r,v,s,v}$) was purchased from ATCC (Rockville, Md.). Cells were cultured in RPMI1640 media supplemented with 10% fetal calf serum and 0.1% gentamycin. Antibody was purified from ascites using Protein G affinity column and concentrated by an ultrafiltration concentrator (Amicon, Danvers, Ma.).

Preparation of labeled antibody $^{123}$I was purchased from Nordion International. Iodination of antibody was performed by a standard chloramine T method.

Transplantation

Donor and recipient mice weighing from 15 to 25 g were anesthetized with chloral hydrate (0.1 ml of a 3.6% solution per 10 g body weight). The left kidney of the donor was mobilized with the ureter. After injection of cold heparinized saline into left renal artery, donor aorta was cut just under the branch of right renal artery. After ligation of appropriate lumber branches, ties were placed around the aorta and vena cava together caudad and individually cephalad to the intended site for the vascular anastomoses. After occlusion of the aorta and vena cava by tightening the loops, longitudinal openings were made in each. The side to end anastomoses between aortas and between donor renal vein and recipient inferior vena cava were performed in running fashion with 10-0 suture. Recipient's left renal artery and vein were ligated together and the kidney was removed. In some animals, the donor ureter was passed under the left vas deferens to reduce the chance of its kinking. Recipient's bladder was opened and the connection was accomplished by using 9-0 nylon suture (Ethicon) in running fashion. The right kidney was removed in some of the experiments.

Scintigraphy

Approximately 100 μCi of 123I-antibody was injected into the tail vein of the recipient mouse 16 hours before scintigraphy. Scintigraphy was performed with a gamma camera (Ohio Nuclear 100) equipped with a 3-mm pinhole collimator as described. For each scintigram, the intensity of radioactivity in the graft was measured in comparison with that in the native kidney after an area of interest had been set by compute planimetry.

Tissue analysis

Mice were killed after scintigraphy. Venous blood was withdrawn and the autologous kidney, transplanted kidney, liver, spleen, heart and lungs were excised. Both kidneys were washed thoroughly with saline. The biodistribution of radioactivity was determined as described. The ratio of percent injected dose per gram of grafted kidney to that of autologous kidney was determined for each mouse.

Animal groups

Twenty-three Balb/c mice were allografted with C3H/He mice kidney. Eighteen of the 23 mice were randomly chosen for scintigraphy 1 to 19 days after transplantation and were injected with radiolabeled antibody and sacrificed thereafter. Another five allografted Balb/c mice were chosen for scintigraphy 3 to 9 days after transplantation. These mice were treated with immunosuppressants as follows: Fifty μl of ascites containing approximately 100 μg of YCD3 antibody was injected ip daily for 4 days starting the day of the first scintigraphy. Cyclosporine (Sandoz, Bazel, Switzerland) (15 mg/kg) was also injected sc daily for two weeks. The second scintigraphy was then performed. The mice were further treated with daily doses of 30 mg/kg of cyclosporine for two weeks. The third scintigraphy was then obtained. Two weeks after the cessation of immunosuppression, the fourth images were taken and they were killed for tissue analysis.

Two C3H/He mice were transplanted with Balb/c kidneys. They were injected with labeled-Y17 antibody at 6 and 8 days after transplantation. Three isografted mice (C3H kidney to C3H recipient), imaged 5, 7 and 21 days after transplantation, served for controls.

In three allografted mice, both native kidneys were removed and donor ureter was connected to the bladder of the recipient. They were imaged on the 3rd, 4th and 5th day of transplantation and killed. Blood samples were taken for measurement of serum creatinine levels. Serum creatinine level was determined by a colorimetric method (Sigma, St. Louis, Mo.).

Histological Examination

Grafted and autologous kidneys were embedded in paraffin and stained with hematoxylin and eosin. The samples were submitted for blinded histopathologic evaluation by two examiners. The extent and severity of lesions were semiquantitatively evaluated on a scale of 0 to 3 (Pirani et al., *Nephron* 1:230–237 (1964)).

Statistical analysis

A $p<0.05$ was considered nonsignificant in comparisons between multiple groups of data. All data were expressed as the mean ± standard deviation. Linear regression was computed by the least squares method.

RESULTS

Scintigraphy and Histopathology

Very good correlations were observed between the graft (G) to native kidney (N) radioactivity (% ID) ratio measured by tissue counting and that measured by computer planimetry from the scintigrams (G/N image=$0.26 \times$G/N tissue+0.71, r=0.90, n=20). G/N ratio obtained from images also correlated well with graft/blood radioactivity (% ID) ratio measured from tissue counting (G/N image=$2.0 \times$graft/blood+1.1, r-=0.95, n=20). Therefore, we used G/N determined by computer planimetry as an index of antibody uptake in the graft in this study.

Figure 21:
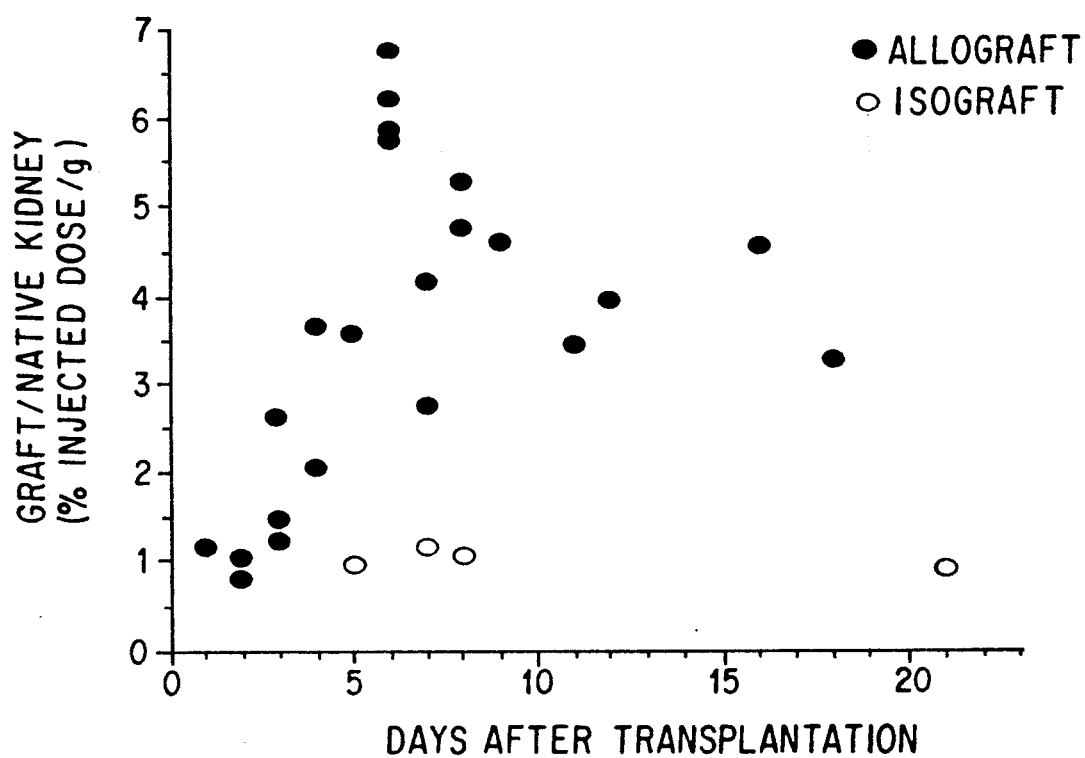
FIG. 21. Time course of Y17 (anti-IE$^k$) monoclonal antibody uptake in kidney allograft.
Figure 22:
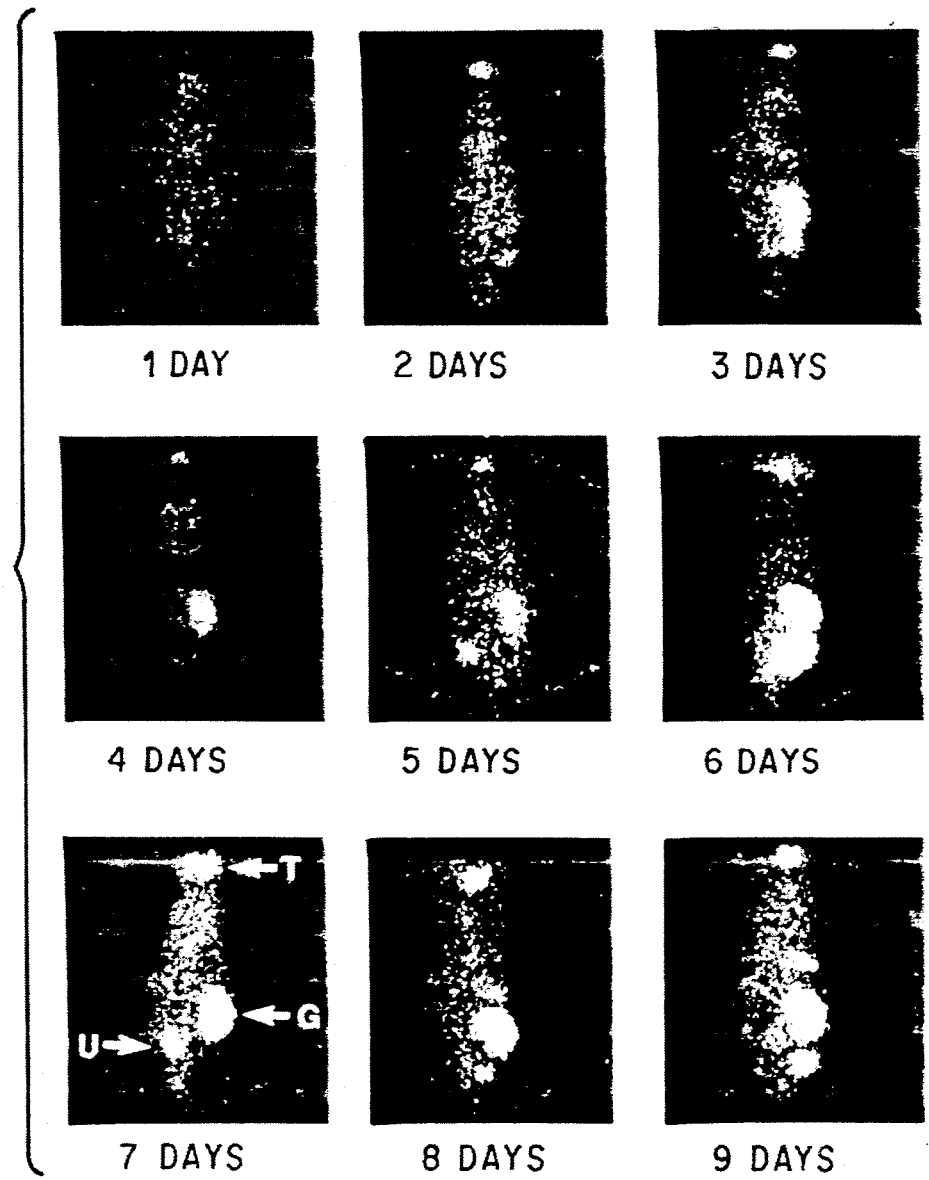
FIG. 22. Temporal changes in anti-MHC class II antibody uptake.

A broad spectrum of histological findings was present, ranging from nearly normal to severe rejection. Regardless of the time after transplantation, radiotracer uptake well reflected histolopathological measurements of the severity of rejection as shown in FIGS. 16 to 20. Radiotracer uptake started to increase from the 3rd day of transplant and formed a peak at around the 6th day, and then reduced gradually (FIG. 21). As shown in FIG. 22, increased radiotracer uptake in the graft could be scintigraphically identified. Mild rejection with only interstitial mononuclear cell infiltrate at the 3rd day of transplantation, showed unequivocal accumulation and could be identified. Isografted mice did not show any increase in radiotracer uptake during the course of observation. C3H recipients allografted with Balb/c heart did not show increase in labeled Y17 antibody uptake, although they showed significant histological changes associated with rejection.

Effects of immunosuppressive therapy

Figure 23:
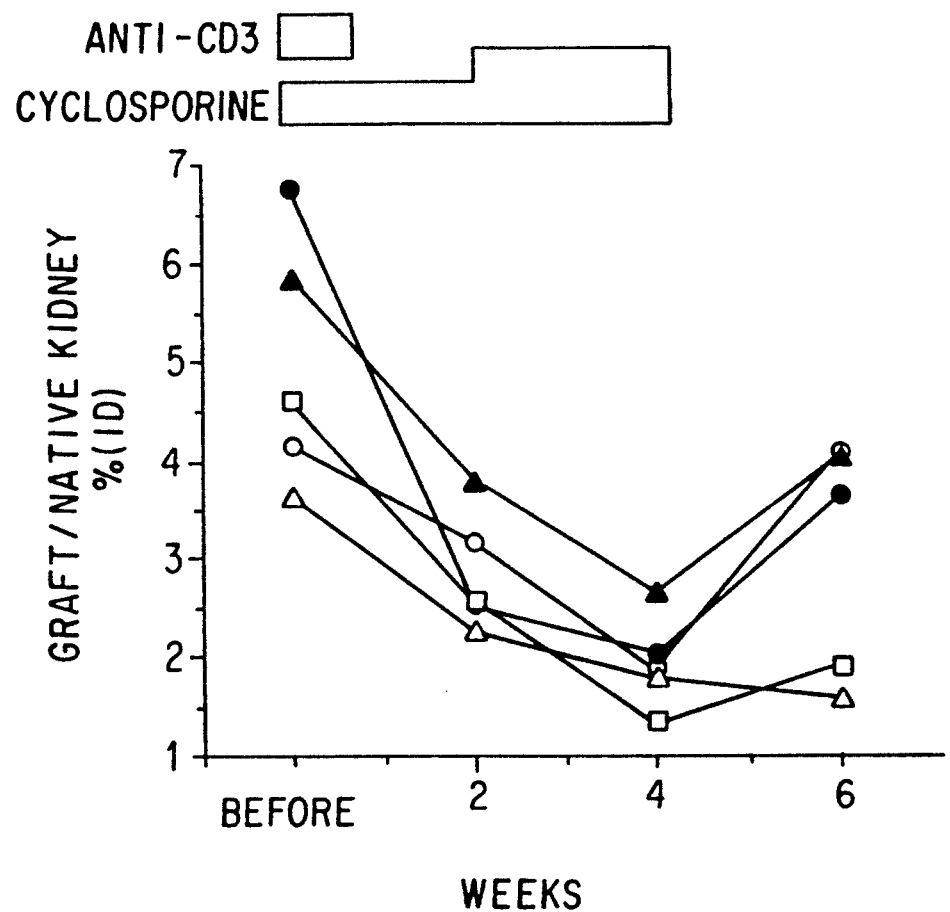
FIG. 23. Effects of immunosuppression on antibody uptake.
Figure 24:
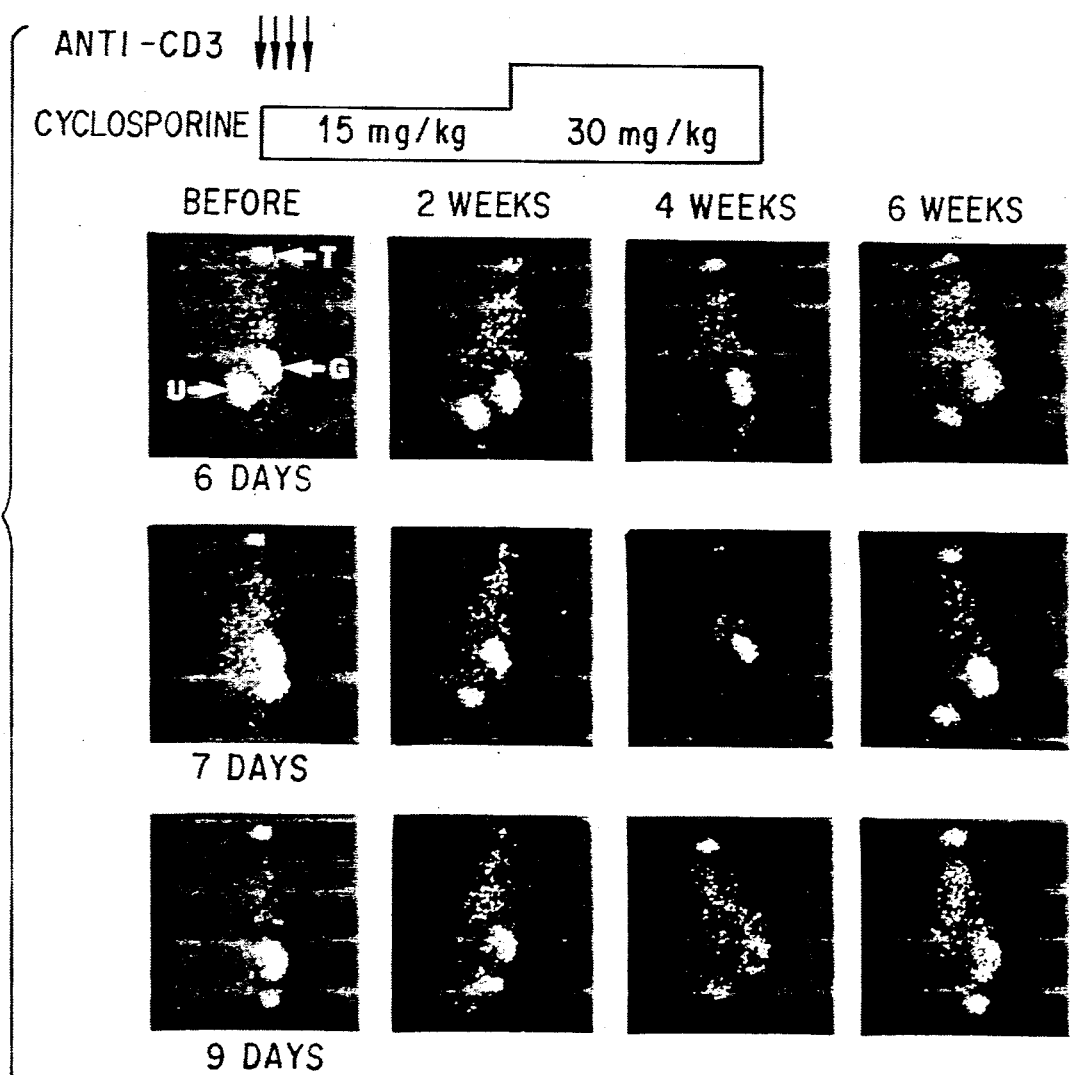
FIG. 24. Effects of immunosuppression on anti-MHC class II antibody uptake.

Five allografted mice imaged at 3, 4, 6, 6, 9 days after operation showed increase in G/N ratio ($5.0 \pm 1.3$). After two weeks of anti-CD3 and cyclosporine therapy, the ratio significantly reduced ($2.9 \pm 0.6$, $p<0.05$ vs. before). After another two weeks of cyclosporine treatment, the ratio further decreased ($1.9 \pm 0.5$, $p<0.01$ vs. 2 weeks). Two weeks after the cessation of treatment, the ratio increased ($3.1 \pm 1.2$, $p<0.05$ vs. 4 weeks) (FIG. 23). These changes in radiotracer uptake could be followed by the scintigraphic images (FIG. 24).

DISCUSSION

These results demonstrate that anti-MHC class II antibody scintigraphy is a sensitive and noninvasive technique to detect early kidney allograft rejection. Noninvasive detection of organ rejection is still a challenging aspect of clinical transplantation. Although a variety of diagnostic methods have been reported, none has gained wide-spread use to date except for the determination of serum creatinine. However, elevation of serum creatinine reflects a decline in graft function, and therefore, cannot be an early marker of rejection. Besides, deterioration of graft function could be caused by many reasons other than rejection, including cyclosporine toxicity. Therefore, a noninvasive technique to detect early rejection in association with rejection process would be desirable.

MHC class I and class II molecules, known as transplantation antigens, play an essential role in the pathogenesis of rejection. Expression of class I antigen appears to depend on species. A large amount of class I antigens are expressed on normal rat kidney, whereas, kidney tissue from normal mouse is negative for class I expression including the renal cortical interstitial dendritic cells (Benson et al., *J. Immunol.* 134:7–9 (1985)). The expression of class II antigens in kidney, however, are demonstrated to parenchymal cells throughout the species reported (Hart et al., *Transplantation* 27:110 (1979); Milton et al., *Transplantation* 41:499–508 (1986)). Human but not rodent vascular endothelial cells normally express class II antigens (Daar et al., *Transplantation* 38:287–298 (1984)). Class II antigens are induced under certain circumstances. They are induced associated with organ rejection, autoimmune injury, viral injection and stimulation by certain cytokines. Massive induction of class II antigens is reported in allografted kidney in mouse (Benson et al., *J. Immunol.* 134:7–9 (1985)), rat (Milton et al., *Transplantation* 41:499–508 (1986)) and human (Hall et al., *Lancet* 1:247–251 (1984)). Once initiated, the cellular infiltrate of the rejection response will release a wide variety of lymphokines into the interstitial connective tissue of the graft. Among these lymphokines γ interferon, which is a potent inducer of class I and class II antigens, acts on the cells in the vicinity to induce these antigens. Then they can become a potential site of attack for the rejection response. These observations obtained by tissue staining gave rise to the rationale to use induced class II antigens as a target of detection of rejection.

Immunoperoxidase Staining

Anti-IA$^k$ antibody 10-2-16 stained myocytes in rejecting allografts (FIG. 6). These findings were significantly different from that obtained with isografts or allografts treated with cyclosporine, in which there was no specific staining. Although we did not quantitatively analyze class II antigen expression in these grafts, antigen expression apparently increased with time after transplantation in nontreated allografts.

Modifications of the above-described modes for carrying out the invention that are obvious to persons of skill in medicine, immunology, pharmacology, and/or related fields are intended to be within the scope of the following claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

We claim:

1. A method for detecting rejection of an allograft in a mammal, said method comprising:
   (a) administering to said mammal an effective amount of a composition comprising at least one monospecific immunoglobulin molecule or fragment thereof diagnostically conjugated to a detectable label, said immunoglobulin or fragment directed against an MHC antigen; and (b) detecting rejection of said allograft, by detecting the presence of said labelled immunoglobulin or fragment.

2. The method of claim 1 wherein said immunoglobulin is directed against MHC Class 2 antigens.

3. The method of claim 1 wherein said immunoglobulin is selected from the group consisting of a monoclonal antibody and a polyclonal antibody.

4. The method of claim 3 wherein said monoclonal antibody is chosen from the group containing anti-HLA DR and W6/32.

5. The method of claim 1 wherein said detectable label is a radioactive isotope.

6. The method of claim 5 wherein said radioactive isotope is chosen from the group consisting of $^{111}$In, $^{99m}$Tc, $^{123}$I, $^{97}$Rv, $^{67}$Cu, $^{67}$Ga, $^{68}$Ga, $^{72}$As, $^{89}$Zr and $^{201}$Tl.

7. The method of claim 1, wherein said allograft is a heart or kidney allograft.

8. The method of claim 7, wherein said allograft is a heart allograft.

9. The method of claim 7, wherein said allograft is a kidney allograft.

10. The method of claim 1 wherein said detectable label is a paramagnetic isotope.

11. The method of claim 10 wherein said paramagnetic isotope is chosen from the group consisting of $^{157}$Ad, $^{55}$Mn, $^{162}$Dy, $^{52}$Cr and $^{56}$Fe.

* * * * *